United States Patent
Tett

(10) Patent No.: US 11,036,283 B2
(45) Date of Patent: Jun. 15, 2021

(54) NAVIGATION CONTROLLER

(71) Applicant: Richard J. Tett, Plano, TX (US)

(72) Inventor: Richard J. Tett, Plano, TX (US)

( * ) Notice: Subject to any disclaimer, the term of this patent is extended or adjusted under 35 U.S.C. 154(b) by 0 days.

(21) Appl. No.: 16/368,342

(22) Filed: Mar. 28, 2019

(65) Prior Publication Data

US 2019/0220086 A1  Jul. 18, 2019

Related U.S. Application Data

(63) Continuation-in-part of application No. 15/874,701, filed on Jan. 18, 2018, now Pat. No. 10,275,019.

(51) Int. Cl.
G06F 3/01 (2006.01)
A61B 5/00 (2006.01)
A61B 5/11 (2006.01)

(52) U.S. Cl.
CPC ............ *G06F 3/011* (2013.01); *A61B 5/1114* (2013.01); *A61B 5/4023* (2013.01); *A61B 5/6895* (2013.01); *A61B 5/6897* (2013.01); *A61B 5/7455* (2013.01); *G06F 3/016* (2013.01); *A61B 5/1118* (2013.01); *A61B 5/1121* (2013.01); *A61B 5/6843* (2013.01); *A61B 5/6844* (2013.01)

(58) Field of Classification Search
CPC combination set(s) only.
See application file for complete search history.

(56) References Cited

U.S. PATENT DOCUMENTS

| 4,817,950 A | 4/1989 | Goo |
| 5,860,861 A | 1/1999 | Lipps et al. |
| 5,864,333 A | 1/1999 | O'Heir |
| 5,872,438 A | 2/1999 | Roston |
| 5,913,684 A * | 6/1999 | Latham .................. G06F 3/011 434/247 |

(Continued)

FOREIGN PATENT DOCUMENTS

| JP | JP 2012221023 A | 11/2012 |
| KR | 20030040732 A | 5/2003 |

(Continued)

OTHER PUBLICATIONS

CH Products, Pro Pedals USB Flight Simulator Pedal, website and product.

(Continued)

*Primary Examiner* — Van N Chow
(74) *Attorney, Agent, or Firm* — David W. Carstens; J. Andrew Reed; Carstens & Cahoon, LLP

(57) ABSTRACT

A device with rotatable footpads for use with interactivity systems and method for same are disclosed. The apparatus may comprise a stanchion for supporting two footpads, wherein the two footpads rotate on an axis passing through the stanchion; a plurality of sensors that detect the rotation of each footpad; and a controller transmitting signals from the plurality of sensors representing the rotation of each footpad to a virtual reality system. The method for using the apparatus may comprise stabilizing footpads by a mechanical means detecting the rotation of the footpads on an axis passing through the footpads via sensors of the footpads that detect rotation of the footpads; and transmitting a digital representation of the rotation of the footpads to a interactivity system.

23 Claims, 11 Drawing Sheets

(56) References Cited

U.S. PATENT DOCUMENTS

| | | | |
|---|---|---|---|
| 6,102,832 A * | 8/2000 | Tani | G06F 3/011 |
| | | | 482/4 |
| 6,351,096 B1 | 2/2002 | Jang | |
| 7,153,242 B2 | 12/2006 | Goffer | |
| 8,398,110 B2 | 3/2013 | Tedla | |
| 8,979,722 B2 | 3/2015 | Klein et al. | |
| 9,081,436 B1 | 7/2015 | Berme et al. | |
| 9,522,324 B2 | 12/2016 | Levasseur et al. | |
| 9,957,006 B2 * | 5/2018 | Tinaphong | B62K 11/007 |
| 2008/0147281 A1 * | 6/2008 | Ishii | B62D 51/005 |
| | | | 701/49 |
| 2008/0261696 A1 | 10/2008 | Yamazaki et al. | |
| 2009/0058855 A1 | 3/2009 | Mishra et al. | |
| 2009/0111670 A1 | 4/2009 | Williams | |
| 2011/0306425 A1 | 12/2011 | Rivard et al. | |
| 2013/0344926 A1 | 12/2013 | Claudel et al. | |
| 2014/0256011 A1 * | 9/2014 | Zelle | C12P 7/10 |
| | | | 435/161 |
| 2017/0144718 A1 * | 5/2017 | Tinaphong | B62K 11/007 |
| 2017/0160793 A1 | 6/2017 | Perlin et al. | |
| 2017/0185168 A1 | 6/2017 | Bonora et al. | |
| 2017/0217529 A1 | 8/2017 | Chen | |
| 2018/0280099 A1 * | 10/2018 | Cone | B25J 13/04 |
| 2018/0326286 A1 | 11/2018 | Rathi et al. | |

FOREIGN PATENT DOCUMENTS

| | | |
|---|---|---|
| KR | 20106-0122611 A | 10/2016 |
| KR | 1796070 B1 | 11/2017 |
| WO | WO 2016042407 A1 | 3/2016 |
| WO | WO 2017184785 A1 | 10/2017 |

OTHER PUBLICATIONS

IKKEGOL, USB Double 2 Foot Switch Control Pedals, product.
Thrustmaster, T150 Force Feedback Racing Wheel and Pedals for PlayStation 4, product.
Amadeo, Ron, "Forget VR Treadmills—Google Patents Motorized, Omnidirectional VR Sneakers", ArsTechnical.com, Nov. 19, 2018, 4 pages.
English Translation of KR 1796070.
English Translation of KR 20106-0122611.
Machine Translation of KR 20030040732.
Machine Translation of JP 2012221023.

* cited by examiner

NAVIGATION CONTROLLER

CROSS-REFERENCE TO RELATED APPLICATION

This application is a continuation-in-part application of U.S. patent application Ser. No. 15/874,701 filed on Jan. 18, 2018, the disclosure of which is incorporated herein by reference.

BACKGROUND OF INVENTION

1. Field of Invention

The present invention relates to display systems, specifically, controllers for interacting with display, entertainment, and/or control systems.

2. Description of Related Art Including Information Disclosed Under 37 C.F.R. 1.97 and 1.98

Virtual reality systems have recently become more and more predominant as visual displays, whether in use with video or electronic games or with other types of visual media. Today, interactive virtual reality systems are becoming a household item, especially with the growth of uses for virtual reality systems. Virtual reality systems can be used not only for video or electronic games, but they can be used for research and educational purposes.

However, problems do persist in the area of virtual reality systems. Because virtual reality systems are meant to visually simulate an environment, users of virtual reality systems have difficulty interacting with these systems while also ensuring their safety in real life. For example, virtual reality users use headsets that generate realistic images and sounds to simulate the users' physical presence in a virtual or imaginary environment. However, in these environments, users want to interact with the virtual or imaginary environment and will physically move to interact with the virtual or imaginary environment. Often, users who move according to a virtual or imaginary environment will encounter an obstacle in real life, and current controllers and devices used for virtual reality do not account for locomotion in real life and in virtual reality.

There are several devices that simulate travel or locomotion in a virtual reality system while the users are stationary. One of which are foot-controlled devices. One representative of this is a product known commonly as the "3dRudder." This product is disclosed in U.S. Pat. Application No. US20170185168 by Bonora, et al and European Pat. Application EP20150798185 (WO 2016042407 A1) by Bonora, et al. While a contribution to the field, the 3dRudder and like devices are disadvantageous in that they require the user to be seated and use their legs and feet together in an unnatural way—especially in the control of rotation—which may lead to back pain and exhaustion. Furthermore, the sense of motion is conveyed only by visual changes in the Virtual Reality and no perception of travel or rotation is conveyed through the feet, legs, body or skin. Although the 3dRudder is capable of moving in several directions, it can only indicate travel in a series of linear vectors, similar to a joystick. It is not possible to travel in an arc, rotate in place, or travel backward in an arc. Inconsistent motion cues between sight and body contributes to disorientation and sickness while navigating a Virtual Reality environment. Additionally, the 3D Rudder does not allow for a user's feet to move independently of one another to trigger a rotation. This product provides movement in a single plane, but offers no capability or option to control vertical ascent/descent.

Another foot-controlled device is disclosed in U.S. Pat. Application No. US2017/0160793 by Perlin, et al. This invention comprises a mat comprising pressure sensitive tiles upon which a user stands and manipulates the distribution of weight to various parts of each foot. The pressure distribution "image" is analyzed and movements forward, backward and sideways may be indicated. Although a user can be trained to use the mat to effect motion in a Virtual Reality system, it is disadvantageous as a virtual vehicle for locomotion for several reasons. Firstly, it is a homogenous surface with no physical attributes typical of a mechanism by which a foot controls acceleration or direction. Secondly, there is no feedback to the feet other than the pushback of the surface, so the user is left to imagine that their feet are moving control surfaces typical of a vehicle. It is well-known that when a person perceives movement through his eyes without any other sensations of movement, they may experience virtual reality sickness with symptoms including headache, disorientation, nausea, etc. Many available devices for VR locomotion, including this one, do not provide active feedback of movement to remediate this problem. Thirdly, the logic by which the mat depressions are interpreted must be calibrated for users based on their weight and foot size.

Other types of currently available devices are disclosed in U.S. Pat. No. 9,522,324 B2 by Levasseur, et al; U.S. Pat. No. 5,864,333 by O'Heir; U.S. Pat. No. 4,817,950 by Goo; U.S. Pat. Application No. US20080261696 by Yamazaki, et al.; U.S. Pat. No. 5,860,861 by Lipps, et al.; U.S. Pat. No. 5,872,438 by Roston; U.S. Pat. Application No. US20130344926 by Claudel, et al.; U.S. Pat. Application No. 20090058855 by Mishra, et al.; U.S. Pat. Application No. 20090111670 by Williams; U.S. Pat. No. 8,979,722 by Klein, et al.; U.S. Pat. No. 8,398,100 by Tedla; and U.S. Pat. Application No. 20110306425 by Rivard, et al.

What is needed is a device that simulates locomotion in a virtual reality system while the user does not physically travel or encounter barriers or does not require restraints (as do omnidirectional treadmills), that rotates in place, and that makes the user feel like he is moving.

BRIEF SUMMARY

Novel aspects of the disclosures are directed to an apparatus with footpads for navigation control in an interactive environment and method for same. In a first embodiment, the navigation controller apparatus comprises two footpads. The two footpads may rotate on an axis or be supported by a mechanical means. The navigation controller apparatus also includes sensors that detect the movement of each footpad. The apparatus includes a computing device that transmits and receives signals from the plurality of sensors representing the rotation of each footpad to a virtual reality system.

In a second embodiment, novel aspects of the present disclosure describe a method for navigation control using a navigation controller apparatus. The method includes the steps of stabilizing two footpads through a mechanical means. Then detecting a movement of said footpads individually or together with a sensor. The signals from the sensor(s) can be transmitted and received by a computing device.

BRIEF DESCRIPTION OF THE DRAWINGS

The present invention will be more fully understood by reference to the following detailed description of the preferred embodiments of the present invention when read in conjunction with the accompanying drawings, wherein.

Figure 1:
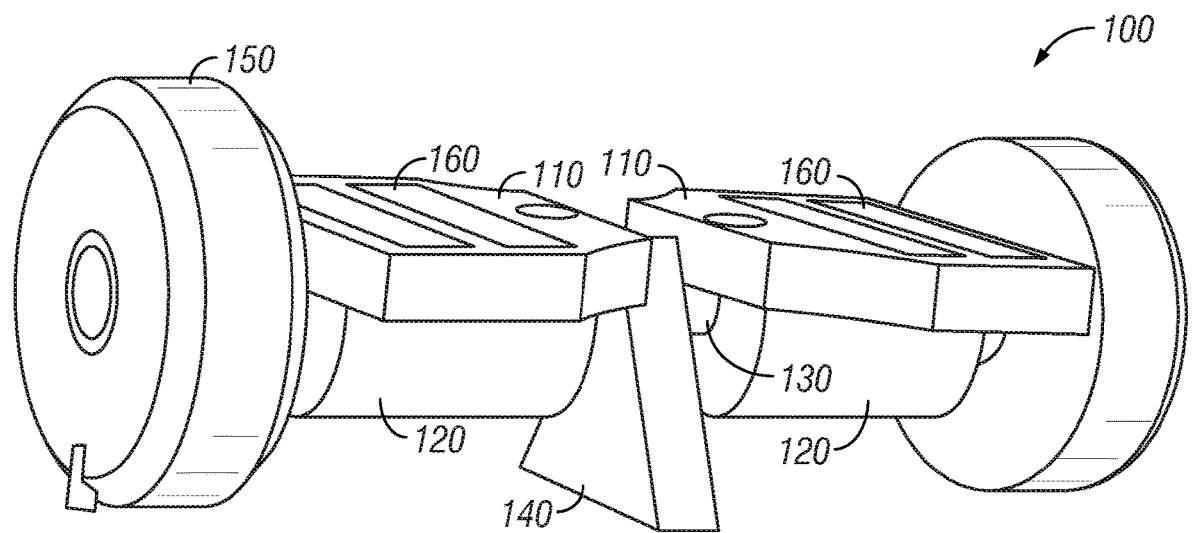
FIG. 1 illustrates a virtual reality locomotion apparatus.

The above figures are provided for the purpose of illustration and description only, and are not intended to define the limits of the disclosed invention. Use of the same reference number in multiple figures is intended to designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION

Several embodiments of Applicant's invention will now be described with reference to the drawings. Unless otherwise noted, like elements will be identified by identical numbers throughout all the figures. The invention illustratively disclosed herein suitably may be practiced in the absence of any element which is not specifically disclosed herein.

FIG. 1 illustrates an exemplary embodiment of a virtual reality locomotion apparatus. In an exemplary embodiment, the virtual reality locomotion apparatus 100 connects to a virtual reality system and simulates locomotion in the virtual reality environment generated by the virtual reality system. The virtual reality locomotion apparatus 100 allows the user to control the locomotion simulation by actuating the various components of the locomotion apparatus 100 to simulate control of virtual reality locomotion. For example, a user can actuate the locomotion apparatus 100 in a certain pattern or orientation to simulate turning left or right in the virtual reality environment.

To operate the exemplary embodiment of the locomotion apparatus 100, the user stands on the footpads 110 of the locomotion apparatus 100. The footpads 110 are disposed on an axle 130 and axial housings 120. The axial housings 120 contain the components for actuating the locomotion apparatus 100. The user can use his feet to actuate the footpads 110, and the footpads 110 and axial supports 120 rotate on the axle 130. The footpads 110 and corresponding axial housings 120 can rotate independently of each other. For example, the left footpad can rotate in an opposite direction from that of the rotational direction of the right footpad. Different rotational orientations of the footpads 110 can simulate changes in direction of locomotion in a virtual reality system.

In an exemplary embodiment, the user can indicate a certain left or right rotation in a virtual reality environment by angling one footpad forward and another footpad backward. For example, to turn counter-clockwise around an axis passing perpendicularly through the center of the device, the user can angle the left footpad down by using the heel of his left foot and can angle the right footpad down by using the ball of his right foot. Similarly, to turn clockwise around an axis passing perpendicularly through the center of the device, the user can angle the left footpad down by using the ball of his left foot and can angle the right footpad down by using the heel of his left foot. Generally, to rotate in either direction, the user can angle the footpads 110 in different and opposite directions to get the correct locomotion rotation in the virtual reality environment.

Additionally, the user can indicate forward or backward motion or locomotion in the virtual reality environment by angling both footpads 110 in a particular direction. For example, to move forward in the virtual reality environment, the user can angle the left footpad and right footpad down by using the balls of both feet, and to move backward in the virtual reality environment, the user can angle the left footpad and right footpad down by using the heels of both feet. If the user angles one footpad more than the other footpad, the user's movement in the virtual reality environment will be in an arc and the front of the user's body in the virtual reality environment will rotate while moving so that the user's body faces the forward direction of the tangent of the arc—whether traveling backward or forward.

In the illustrative embodiment of FIG. 1, the axle 130 is disposed on a stanchion 140 that serves to support the axle 130 and accordingly the weight of the user when he stands on the locomotion apparatus 100. The manner in which the axle 130 passes through and supported by the stanchion 140 is dictated by the connection means between the axle 130 and the stanchion 140. For example, the stanchion 140 can comprise a mount upon which the axle sits and rotates. The connection between the axle 130 and the stanchion 140 can use any other currently available or later developed technology for connecting the two components.

The present exemplary embodiment comprises a stanchion 140 disposed between the footpads. However, in other embodiments, more than one stanchion can be used to support the weight of the users, and stanchions can comprise any arrangement to support the axle 130 and the locomotion apparatus 100. For example, a stanchion can be placed on each end of the locomotion apparatus 100 instead of between the footpads 110. Such stanchion arrangement can provide more support to the apparatus 100 when a user stands on the locomotion apparatus 100. Further, the stanchion 140 can have any shape to accommodate supporting the axle 130 and the footpads 110.

Also shown in the illustrative embodiment of FIG. 1 are wheels 150 that serve to give impression of locomotion. These wheels 150 can also act as stanchions to support the locomotion apparatus 100 when a user stands on the footpads 110.

In one embodiment, strips 160 are disposed of on the top side of the footpads, and these strips 160 are meant to provide friction and stability to the user as he stands on the footpads. Another embodiment uses the strips 160 as sensors, which are discussed in detail below.

The operation of the locomotion apparatus 100 is based on the detection of changes in the footpads 110 by sensors and actuation of motors and environmental simulators in response. These sensors (not illustrated) and motors (not illustrated) can be disposed inside the locomotion apparatus, i.e., inside the footpads 110, the axial housings 120, the stanchion 140, or the wheels 150. Information from the sensors and to the motors are processed by a processor (not illustrated) also disposed inside the locomotion apparatus, and an I/O controller manages the communication between the processor, the sensor, and motors. The processor and the I/O controller can also manage communication from the locomotion apparatus to the virtual reality system. More detail about these components of the locomotion apparatus is discussed below.

Figure 2:
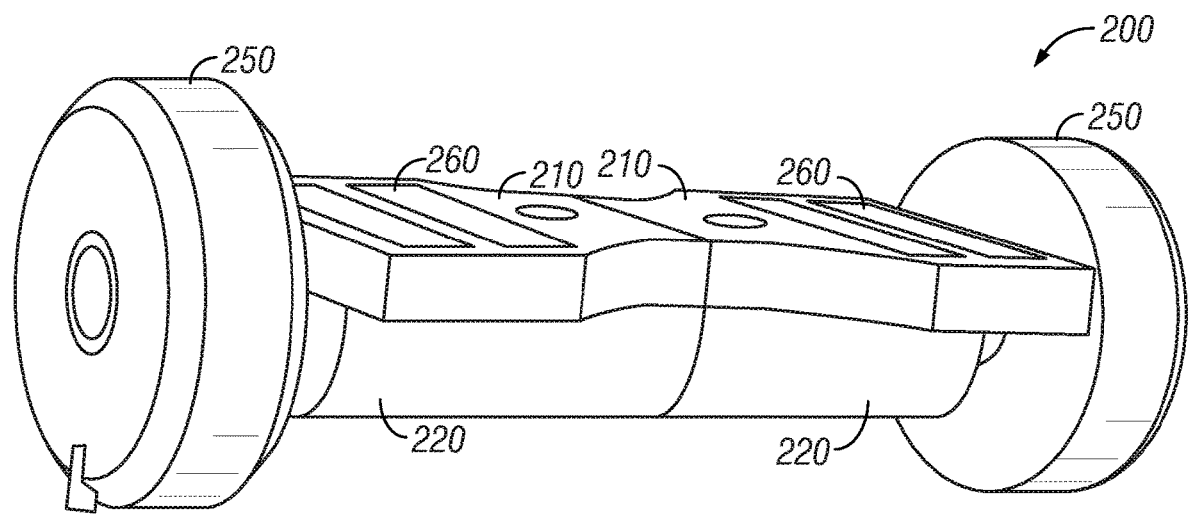
FIG. 2 illustrates the virtual reality locomotion apparatus.

FIG. 2 illustrates a perspective view of an exemplary embodiment of the virtual reality locomotion apparatus. In this illustrative embodiment, the wheels 250 act as stanchions that keep the locomotion apparatus 200 stationary and support the weight of the user during use of the locomotion apparatus 200. In the present exemplary embodiment, the footpads 210 and the axial housings 220 are designed and shaped to meet at a central plane bisecting the locomotion into two symmetrical halves. Similar to the embodiment of FIG. 1, the present exemplary embodiment comprises an axle (not illustrated) that passes through the axial housings 220 and connects the two wheel stanchions 250. The axle is designed to connect to the center of the wheel stanchions 250. The footpads 210 and axial housings 220 can still rotate independently while disposed on the axle.

Figure 3:
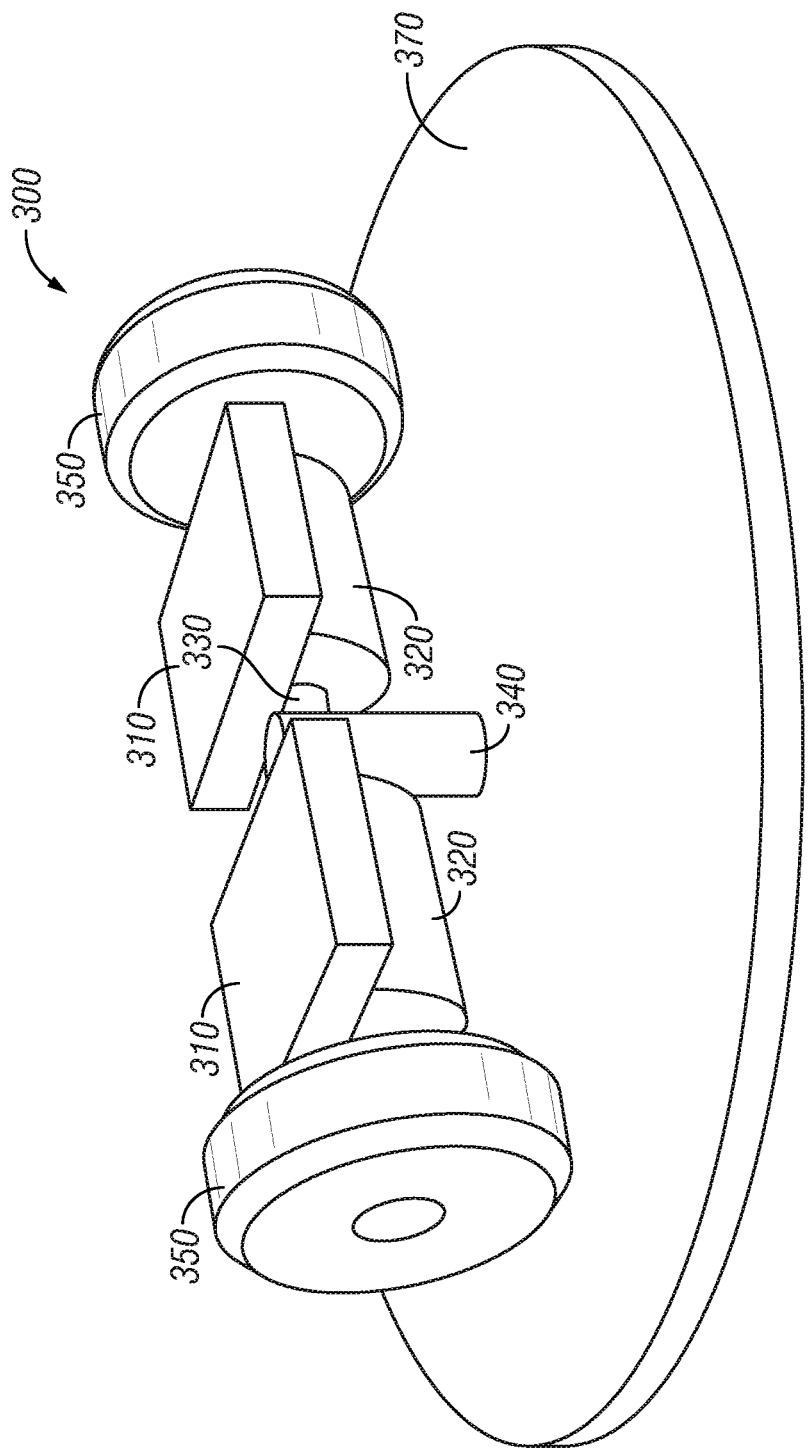
FIG. 3 illustrates a perspective view of the virtual reality locomotion apparatus on a rotatable platform.

FIG. 3 illustrates a perspective view of an exemplary embodiment of the virtual reality locomotion apparatus on a platform. In the present exemplary embodiment, the locomotion apparatus 300 rotates around a fixed point (the fixed point being the central pivot 340), and the user is able to feel the movement of the locomotion apparatus 300 around the fixed point on the platform 370. Because the locomotion apparatus 300 is fixed to the platform 370, the user will not encounter any obstacles in real life. In the present exemplary embodiment, the wheels 350 act to support the user's weight and the central pivot 340 serves to keep the locomotion apparatus 300 connected to and attached to the platform 370. The central pivot 340 rotates on an axis perpendicular to the platform 370 and that passes through the center of the platform 370. The rotation of the footpads 310 in particular orientations actuate the rotation of locomotion apparatus 300 around the axis through which the central pivot 340 passes. Actuating the rotation of the locomotion apparatus can include actuating the wheels 350 in a certain orientation corresponding to the orientation of the footpads 310 by the user.

In an exemplary embodiment, the user can indicate a certain left or right rotation in a virtual reality environment by angling one footpad forward and another footpad backward and for rotation of the locomotion apparatus 300. For example, to rotate counterclockwise, the user can angle the left footpad down by using the heel of his left foot and can angle the right footpad down by using the balls of his right foot. Similarly, to rotate clockwise, the user can angle the left footpad down by using the balls of his left foot and can angle the right footpad down by using the heel of his left foot. Generally, to rotate in either direction, the user can angle the footpads 310 in different and opposite directions to get the correct locomotion rotation in the virtual reality environment and to actuate the rotation the locomotion apparatus 300.

The present exemplary embodiment can be used to indicate a forward or backward motion or locomotion using similar footpad orientations as the illustrative embodiments of FIGS. 1 and 2. For example, to move forward in the virtual reality environment, the user can angle the left footpad and right footpad down by using the balls of both feet, and to move backward in the virtual reality environment, the user can angle the left footpad and right footpad down by using the heels of both feel. However, because the locomotion apparatus 300 of the present exemplary embodiment is fixed in position by the central pivot 340, the user will not be able to experience or feel any forward or backward motion of the locomotion apparatus 300 itself in real life. Forward and backward motion or locomotion in the virtual reality environment can still be simulated by environmental simulators which are discussed below.

Since the apparatus 300 can travel in an arc when the footpads 310 are angled to different degrees, but in the same direction (either forward or backward). The rotation of the apparatus 300 (and the user's body) will correspond to the tangent of the arc on which the user is 'traveling' in the virtual environment.

In one embodiment, the rotation of the user is controlled by output of the virtual reality system rather than by an autonomous action of the apparatus 300 in response to the foot movements. This enables support of a possible situation in virtual reality where the "movement of the user" is blocked in the virtual environment due to an obstacle and the rotation of the user should correspondingly be blocked. A short motor action back and forth may be actuated to simulate hitting the obstacle.

Figure 4:
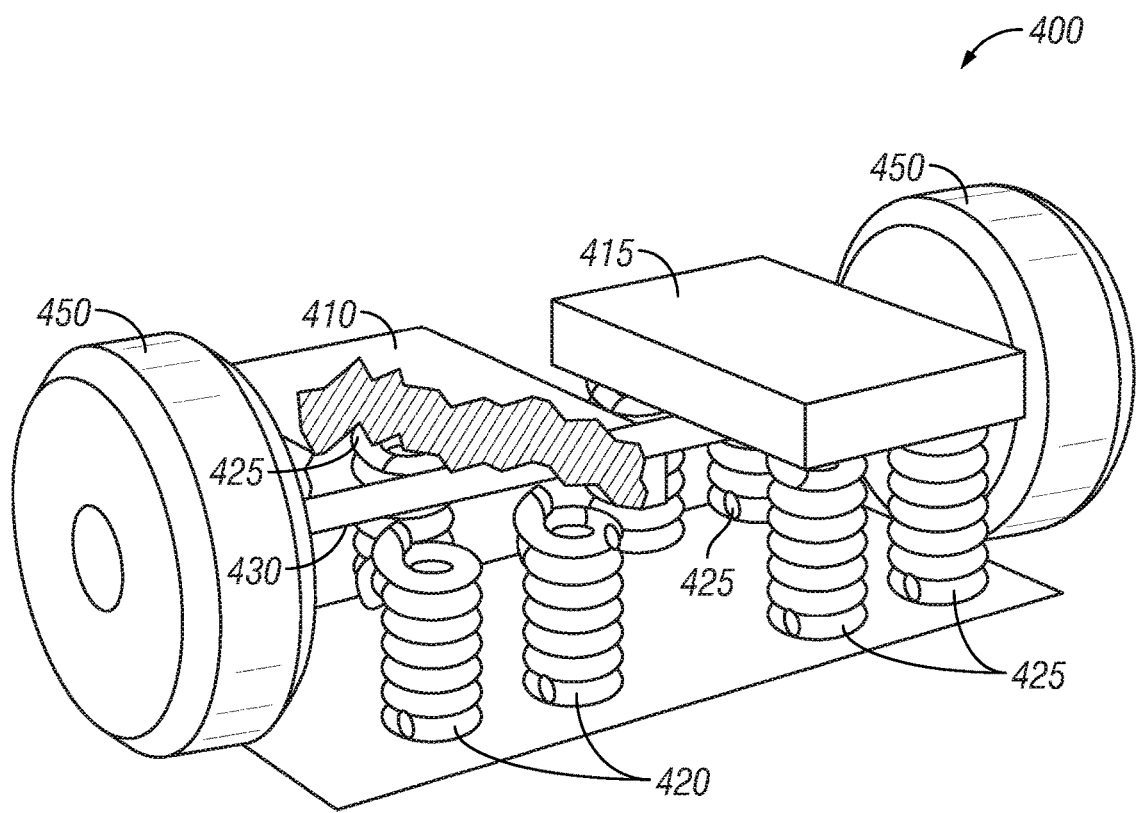
FIG. 4 illustrates a perspective and partially cut-away view of the virtual reality locomotion apparatus.

FIG. 4 illustrates a perspective and partially cut-away view of an exemplary embodiment of the virtual reality locomotion apparatus. Similar to the embodiment of FIG. 1, the wheels 450 are optionally non-functional and give the impression of motion and locomotion to the user. The user interacts with the footpads 410 and 415 to create any motion or locomotion in the virtual reality system, and the footpads 410 and 415 in the present exemplary embodiment are supported by springs 420 and 425 for footpads 410 and 415 respectively. The user can actuate the footpads 410 and 415 in a similar manner as the footpads 100 in FIG. 1. For example, to turn left, the user can angle the left footpad down by using the heel of his left foot and can angle the right footpad down by using the balls of his right foot. Similarly, to turn right, the user can angle the left footpad down by using the balls of his left foot and can angle the right footpad down by using the heel of his left foot. The angling of the footpads creates a vertical downward force against the springs 420 and 425 upon which the footpads 410 and 415 are disposed.

The force on the springs 420 and 425 can be detected by sensors (not illustrated). In one embodiment, the springs 420 and 425 themselves can be sensors via being piezo-electric, and any force exerted on them can be transformed into an electrical signal that can be interpreted by a processor. In another embodiment, the springs 420 and 425 are located on top of sensors, which can be piezo-electric sensors, and the sensors detects any changes in vertical downward force on the springs 420 and 425, which then are then sent to a processor for interpretation.

Any number of springs 420 and 425 and arrangement thereof can be used for the footpads 410 and 415. The present exemplary embodiment includes four springs 420 for footpad 410 and four springs 425 for footpad 415. The springs 420 for footpad 410 are positioned near the four corners of the footpad 410 (not all springs illustrated) and the springs 425 for footpad 415 may be positioned near the four corners of the footpad 415 (not all springs illustrated).

In the present exemplary embodiment, the footpads 410 and 415 are connected to the wheels 450 by an axle 430, and in other embodiments, the footpads 410 and 415 are connected to the wheels by other currently available or later existing mechanisms for connecting these components. The axle connects the centers of the wheels 450 and is disposed on the bottom sides of the footpads 410 and 415. The axle stabilizes the two footpads and in one embodiment, the footpads 410 and 415 can rotate around the axis formed by the axle 430. In one embodiment, the footpads 410 and 415 comprises ports on the bottom sides of the footpads 410 and 415 through which the axle 430 passes, and thereby allowing for rotation of the footpads 410 and 415 on the axle 430. Optionally, axial housings similar to those shown in FIGS. 1-3 can be incorporated with the footpads 410 and 415 to accommodate the axle 430.

In an additional embodiment, each footpad 410 and 415 can be supported by a footpad pivot (not illustrated). These footpad pivots allow the footpads 410 and 415 to tilt in any direction while the footpads 410 and 415 are supported by the springs 521-524, and 526-529, or any currently available or later developed means of supporting the footpads 410 and 415. These footpad pivots are shaped to allow for the tilting of the footpads 410 and 415, such as a pyramid, cone, or post, and these footpad pivots can connect to the footpads 410 and 415 via a ball joint mechanism.

Figure 5:
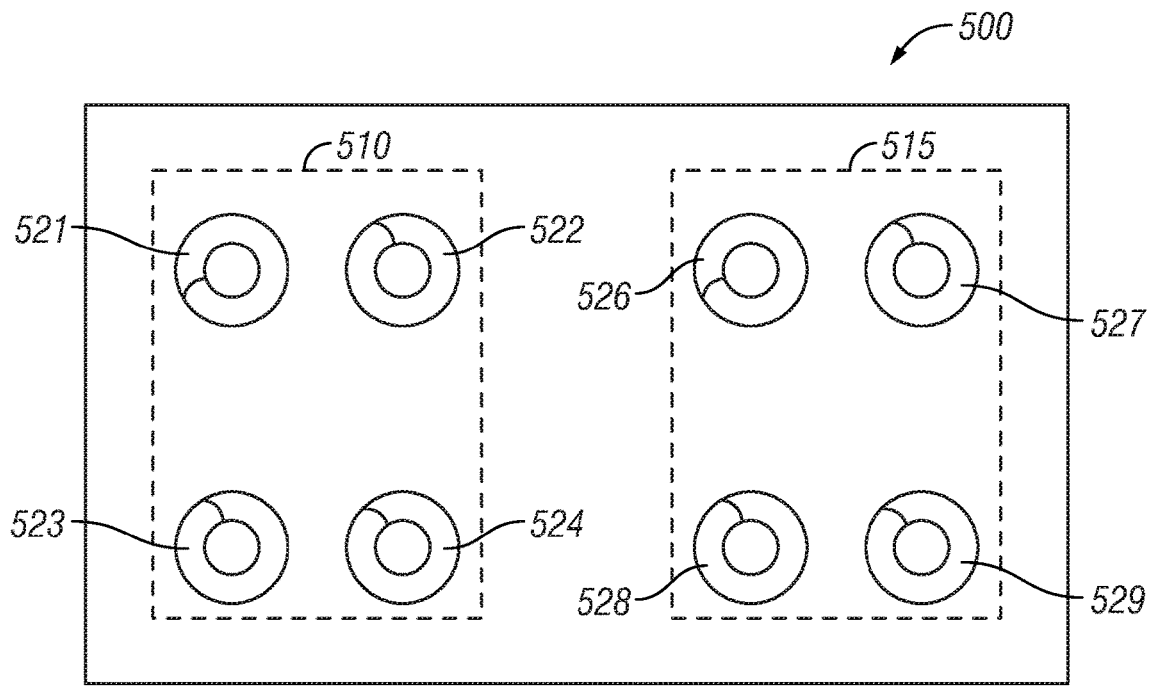
FIG. 5 illustrates a top and partially cut-away view of an exemplary embodiment of the virtual reality locomotion apparatus.

FIG. 5 illustrates a top view of an exemplary embodiment of the virtual reality locomotion apparatus. FIG. 5 illustrates the footpads 510 and 515 in dotted lines so the placement of the springs 521-524, and 526-529 underneath the footpads 510 and 515 are more clearly defined. As mentioned with regards to the exemplary embodiment illustrated in FIG. 4, the springs 521-524, and 526-529 are located near the corners of the footpads 510 and 515.

Sensors (not illustrated) connected to the springs 521-524, and 526-529 detect any changes in the pressure or force exerted against the springs 521-524, and 526-529. In an exemplary embodiment, the sensors can detect changes in pressure or force exerted on the springs and transmit these detected changes in pressure or force to a virtual reality system, and the virtual reality system will in turn affect the user's visual display of the virtual reality environment according to the below Table 1:

TABLE 1

| Motion in Virtual Reality Environment | Left Footpad 510 | Right Footpad 515 |
| --- | --- | --- |
| Rotate Counterclockwise | 523 + 524 | 526 + 527 |
| Rotate Clockwise | 521 + 522 | 528 + 529 |
| Forward | 521 + 522 | 526 + 527 |
| Reverse/Backward | 523 + 524 | 528 + 529 |
| Ascending | 522 + 524 | 527 + 529 |
| Descending | 521 + 523 | 526 + 528 |

Any combination or arrangement of sensors and/or springs may be used to effectuate different motions and locomotion in a virtual reality environment, and Table 1 and FIG. 5 provide an example of a combination and arrangement of sensors and/or springs in an exemplary embodiment.

Figure 6:
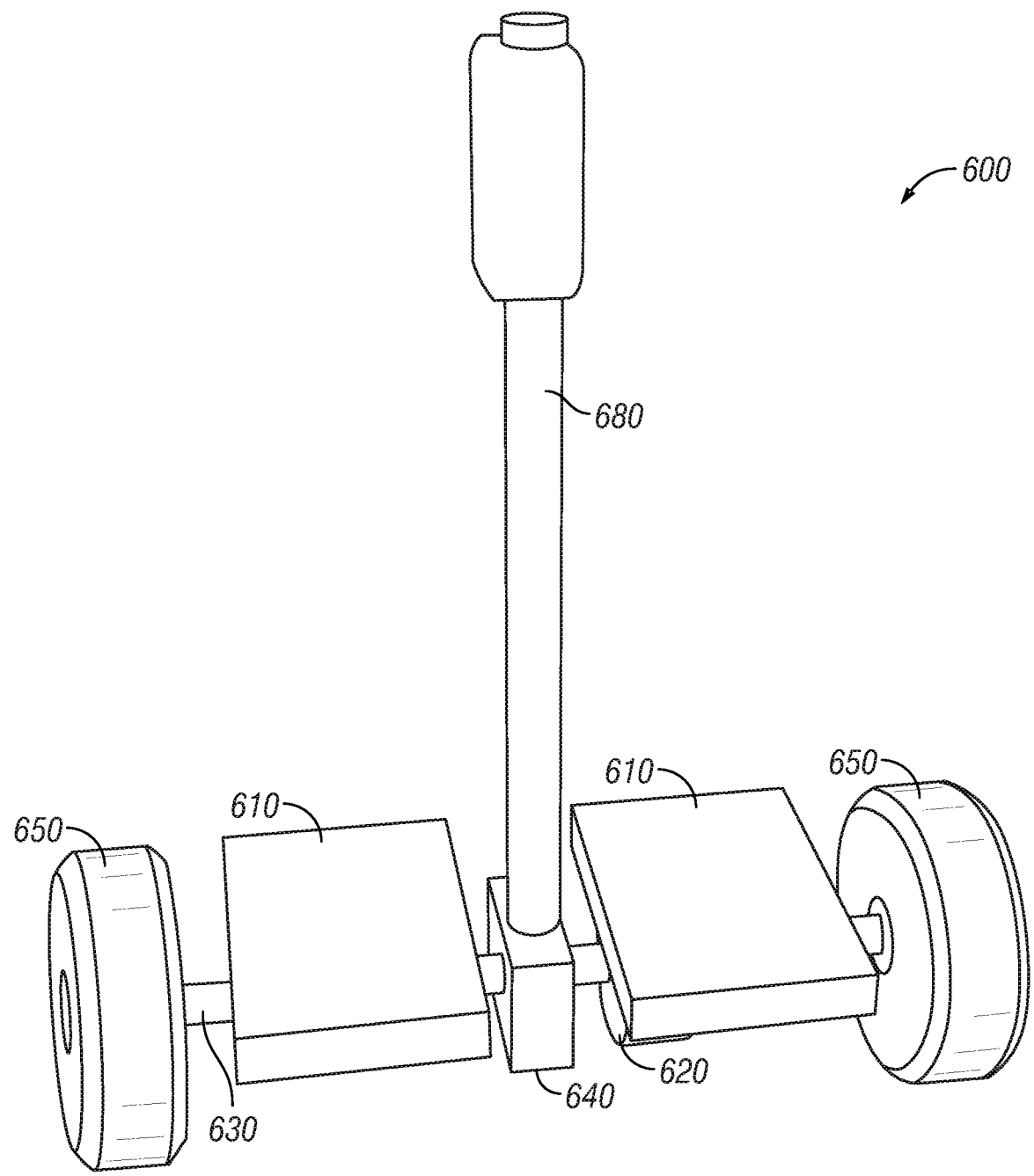
FIG. 6 is a perspective view of the virtual reality locomotion apparatus.

FIG. 6 is a perspective view of an exemplary embodiment of the virtual reality locomotion apparatus. This present exemplary embodiment of the virtual reality locomotion apparatus 600, like FIGS. 1-3, includes footpads 610 and axial housings 620 that rotate around an axle 630. The axle 630 passes through and is stabilized by the central stanchion 640, and optionally, the axle 630 can be stabilized by wheels 650 that can act as additional support for the locomotion apparatus 600. This present exemplary embodiment includes a central joystick 680 that a user can use to affect the visual display from the virtual reality system.

In one embodiment, the central joystick 680 is disposed on the central stanchion 640, and the connection between the central joystick 680 and the central stanchion 640 can comprise a ball-joint mechanism that detects any changes in orientation of the central joystick 680. A ball-joint mechanism for the joystick 680 allows the user to manipulate the user's visual display from the virtual reality system.

In another embodiment, the central joystick 680 passes through the central stanchion 640 and is disposed on the axle 630, and accordingly the central joystick 680 rotates on the axle 630 and around the axis through which the axle 630 passes. The rotation of the central joystick 680 can simulate ascent and descent of the user in the virtual reality environment, or can allow the user to manipulate the user's visual display from the virtual reality system.

While the present exemplary embodiment includes the central joystick 680 disposed between the footpads 610, in yet another embodiment, the locomotion apparatus 600 can include more than one joystick for use and operation by the user. Joysticks can be disposed on the stanchions at the ends of the locomotion apparatus 600, and any number of joysticks can be used with the locomotion apparatus 600.

Any currently available or later developed mechanism for connecting the central joystick 680 to the central stanchion 640 or to the axle 630 may be used, and any currently available or later developed sensor technology may be used to detect any motion or movement of the central joystick 680. Furthermore, the present exemplary embodiment of FIG. 6 can incorporate any features, principles, and/or techniques used with the exemplary embodiments of FIGS. 1-5.

Figure 7:
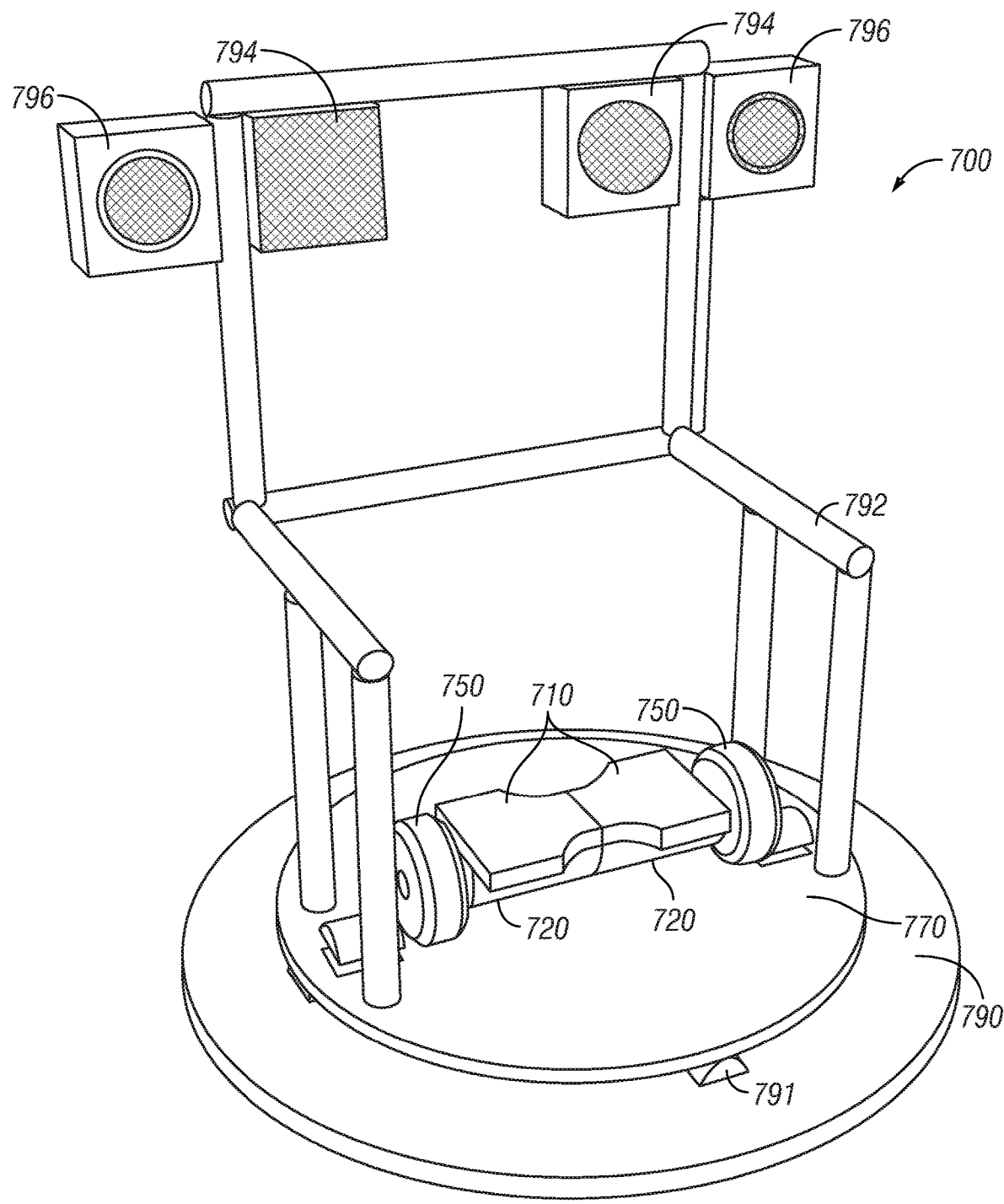
FIG. 7 illustrates the virtual reality locomotion apparatus with environmental simulators.

FIG. 7 illustrates an exemplary embodiment of the virtual reality locomotion apparatus with environmental simulators. The illustrative embodiment of FIG. 7 is similar to the exemplary embodiment of FIG. 3 in that FIG. 7 illustrate a locomotion apparatus 700 fixed to a platform 770 by a wheel stanchions 750. The present exemplary embodiment of the locomotion apparatus 700 does not rotate on top of the platform 770 like the locomotion apparatus of FIG. 3. Instead, the platform 770 rotates on a base 790 so that the user can feel the locomotion or motion displayed in the virtual reality environment in real life. The platform 770 is fixed to the base 790 by the wheel stanchions 750 or any other currently available or later developed mechanism for affixing the platform 770 to the base 790, so that the platform 770 can rotate around an axis passing through the central pivot 740. The exemplary embodiment includes rollers 791 disposed between the base 790 and the platform 770. These rollers 791 actuate when the user changes the orientation of the footpads 710. Any currently available or later developed mechanism for rotating the platform 770 on the base 790 can be used for the exemplary embodiment.

As mentioned with FIG. 3, the user can indicate a certain left or right rotation in a virtual reality environment by angling one footpad forward and another footpad backward and for rotation of the locomotion apparatus 700. For example, to turn left, the user can angle the left footpad down by using the heel of his left foot and can angle the right footpad down by using the balls of his right foot. Similarly, to turn right, the user can angle the left footpad down by using the balls of his left foot and can angle the right footpad down by using the heel of his left foot. Generally, to turn in any direction, the user can angle the footpads 710 in different and opposite directions to get the correct locomotion rotation in the virtual reality environment and to actuate the rotation of the platform 770 on the base 790.

Further, the present exemplary embodiment comprises environmental simulators supported on a frame 792 disposed on the platform 770. The frame 792 can be shaped and oriented in any configuration. In another embodiment, the frame 792 can be disposed on the base 790 instead of the platform 770 and environmental simulators can located anywhere on the frame surrounding the user and the platform 770 to give the user as close to a full-immersion experience with the virtual reality system.

The environmental simulators can comprise fans 794 and speakers 796 that provide real-life sensations to the user of the virtual reality environment. For example, the fans 794 can provides a touch-based sensory input to the user: while the virtual reality system cannot simulate any touch-based input, the fans 794 can actuate so that the user can visual the effects of wind and can feel air circulation on his wind that emulates the wind of the virtual reality environment. Similarly, where the virtual reality system does not provide any audio device such as headphones, the speakers 796 of the present exemplary embodiment can provide audio-based input.

Figure 8:
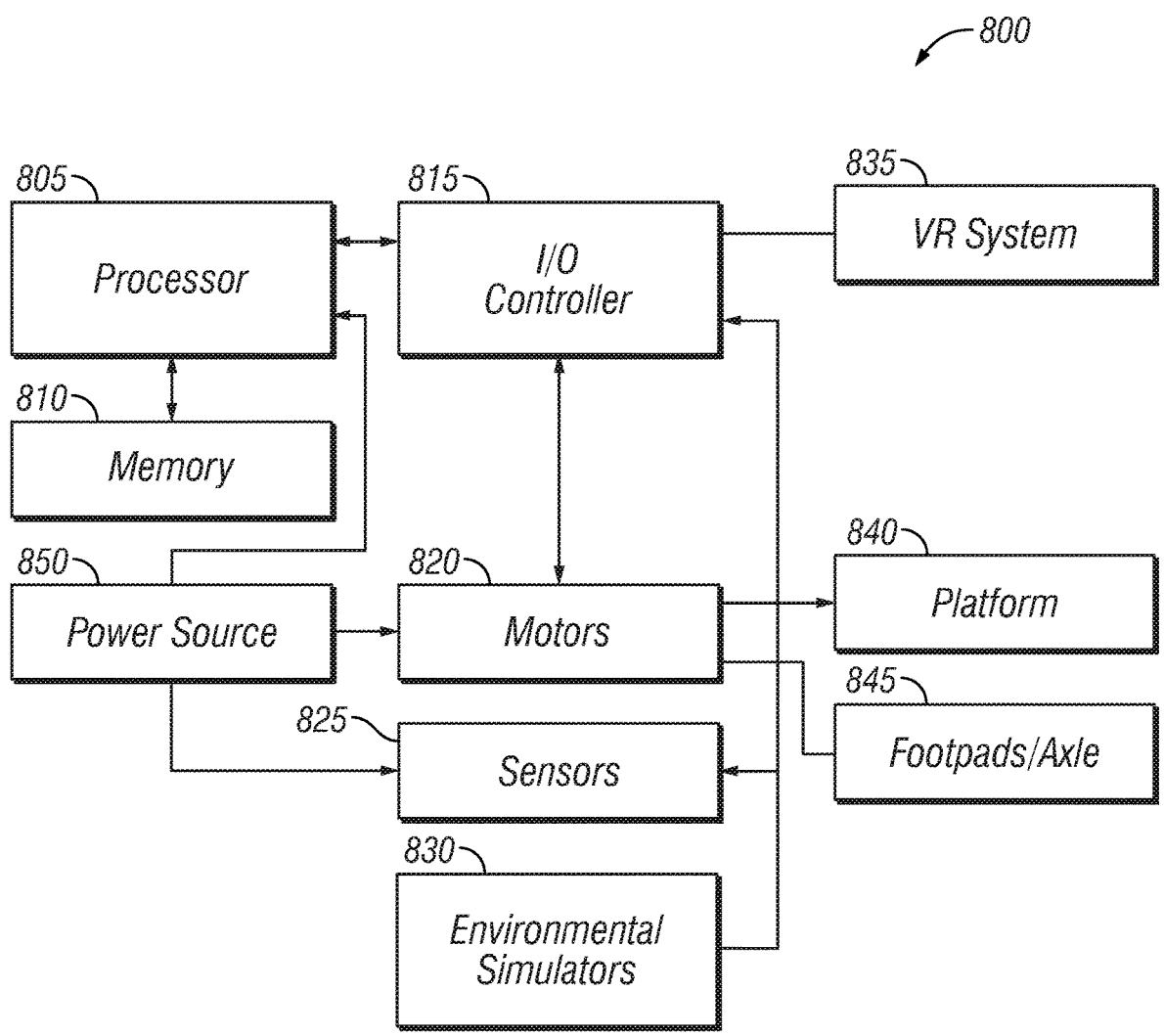
FIG. 8 illustrates a block diagram of components of the virtual reality locomotion apparatus.

FIG. 8 illustrates a block diagram of components of an exemplary embodiment of the virtual reality locomotion apparatus. In an exemplary embodiment, the virtual reality locomotion apparatus 800 can be controlled by a processor 805 connected to memory 810, which includes readable computer instructions for the processor 805. The processor 805 communicates with an I/O (input/output) controller 815 that manages the input and output signals to the various input and output devices and controllers of the virtual reality locomotion apparatus 800. These input and out devices include the motor 820, sensors 825, and environmental simulators 830. The I/O controller 815 also manages communication with the virtual reality (VR) system 835, and the communication can be through a wired connection or through a wireless connection. Additionally, a power source 850 is included in the locomotion apparatus 800 so as to supply power to various components, and the power source may be a battery or an AC adapter. In an exemplary embodiment, the virtual reality locomotion apparatus 800 contains a subset of these components. For example, the processor 805, memory 810, I/O controller 815, motor 820, sensors 825, and environmental simulators 830 are contained inside the virtual reality locomotion apparatus 800 as disclosed previously. Some environmental simulators 830, the platform 840, the power source 850, and the VR system 835 are components that are not contained inside the locomotion apparatus 800 in some exemplary embodiments.

The processor 805 reads computer-readable instructions from memory 810 and upon input from the VR system 835 through the I/O controller 815, transmits actuation signals to various input and output devices through the I/O controller 815. The processor 805 through the I/O controller 815 controls the motor 820, speakers 825, and environmental simulators 830. The processor 805 in turn through the I/O controller 815 receives information from the sensors 825, and then after processing information from these devices, passes the information through the I/O controller 815 to the VR system 835. The information received by the I/O controller 815 may be wired or wireless. One of ordinary skill in the art would understand how to select, program, and use the processor 805, memory 810, and I/O controller 815 for the locomotion apparatus 800 as disclosed herein.

As mentioned previously, the motor 820 is controlled by the processor 805 through the I/O controller 815. The motor 820 automates and actuates the virtual reality locomotion apparatus 800. In one embodiment, the motor 820 can actuate the axle or the footpads 845 of the locomotion apparatus 800 to stabilize the footpads 845 for use by the user. In another embodiment, the motor 820 actuates the rotation of the locomotion apparatus 800 on a platform 840, such as in the locomotion apparatus of FIG. 3. The motor 820 can actuate the movements and rotation of the footpads and/or axle 845. In yet another embodiment, the motor 820 actuates the rotation of the platform 840 on the base 790 as shown in FIG. 7, and the footpads are stabilized in the nominal parallel position by springs and/or solenoids. The locomotion apparatus 800 can comprise any number of motors to actuate its various components. One of ordinary skill in the art would understand how to choose and implement the motors for the locomotion apparatus 800.

As mentioned previously, the sensors detect changes in the footpads of the locomotion apparatus 800 and transmits signals to the processor 805 through the I/O controller 815. The sensors 820 can include gyroscopes, piezo-electric sensors, and any other type of sensors, currently available, or later developed, that can be used to detected changes in the footpads of the locomotion apparatus 800. One of ordinary skill in the art would understand how to choose and implement sensors 820 for the locomotion apparatus 800.

Also mentioned previously, the environmental simulators 830 are controlled by the processor. The environmental simulators 830 can include vibrators, fans, speakers, and any other device that can be used to simulate in real-life the actions, sounds, and environment inside the virtual reality environment. One of ordinary skill in the art would know and understand how to implement the environmental simulators 830 for the locomotion apparatus 800 in response to input and output from the virtual reality system 835.

Figure 9:
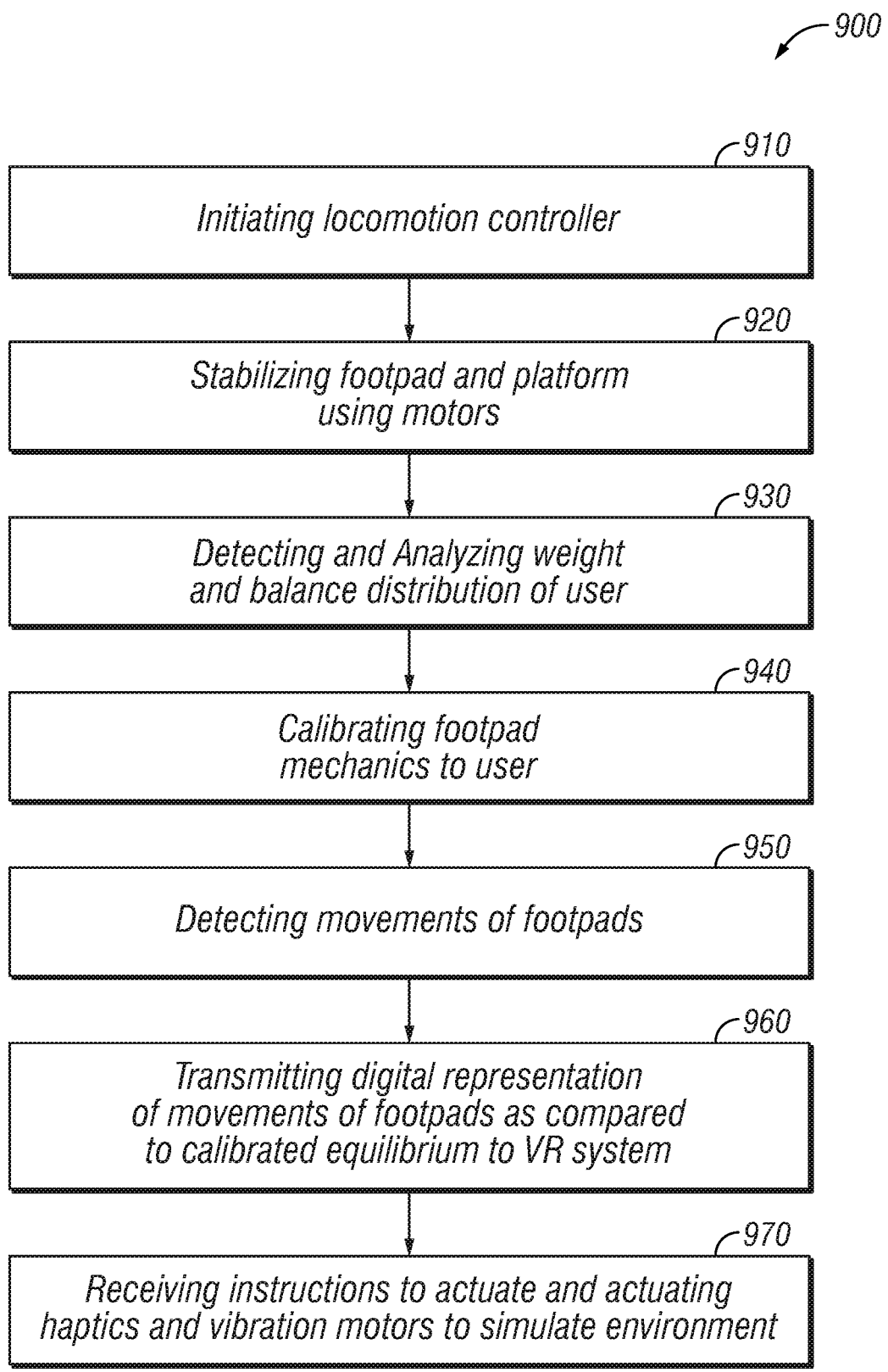
FIG. 9 is a flowchart of a process for using the virtual reality locomotion apparatus with a virtual reality system.

FIG. 9 is a flowchart of a process for using the virtual reality locomotion apparatus with a virtual reality system. The steps of flowchart 900 may be implemented by a virtual reality locomotion apparatus, such as the virtual reality locomotion apparatus exemplified in and disclosed in FIGS. 1-8.

The process begins by initializing the locomotion apparatus (step 910). The user can press a power button that will begin initializing the processor and other components of the locomotion apparatus.

Once the locomotion apparatus is initialized, the footpads and platform are stabilized using motors, solenoids, or springs of the locomotion apparatus (step 920). Users may leave the footpads at an angle to the ground or to the platform, or the platform may be rotated away from its initial position on the base. Accordingly, the locomotion apparatus resets the position of the footpads and platform to their original and/or initial orientation and position. Resetting the footpads and platform allows a user to more easily mount the locomotion apparatus.

Once the footpad and platform are stabilized, a user can stand on the locomotion apparatus and the locomotion apparatus detects and analyzes the weight and balance distribution of the user on the locomotion apparatus (step 930). Because each user is different, the locomotion apparatus detects how the user stands on the locomotion apparatus by detecting the weight and balance distribution of the user on the sensors and/or springs of the locomotion apparatus.

Then, the locomotion apparatus calibrates the footpad mechanics to the user (step 940). Using the detected and analyzed weight and balance distribution of the user from step 930, the locomotion apparatus calibrates the footpad mechanics to respond to the user. Changes in the pressure of the footpads can differ so the locomotion apparatus calibrates these changes in motion for users.

The user can then operate the locomotion apparatus using their feet in response to a visual display by the virtual reality system, and the locomotion apparatus detects movements of the footpads (step 950). As mentioned previously, the locomotion apparatus detects the movements of the footpads using sensors.

The locomotion apparatus transmits a digital representation of the rotation of the footpads to the virtual reality system (step 960), and this digital representation may be in comparison to the calibrated equilibrium determined by the locomotion apparatus in step 930. The digital representation is generated based on signals from the sensors of the locomotion apparatus, and the digital representation can be customized based on the virtual reality system used with the locomotion apparatus.

The locomotion apparatus then receives instructions from the virtual reality system to actuate various components, and the locomotion apparatus actuates environmental simulators in response to the instructions from the virtual reality system (step 970). The instructions from the virtual reality system can include instructions to actuate some of the environmental simulators of the locomotion apparatus, such as vibrators, fans, speakers, and any other device that can be used to simulate in real-life actions and things in a virtual reality environment. The locomotion apparatus can be implemented to interface with any currently available or later developed virtual reality system.

Figure 10A:
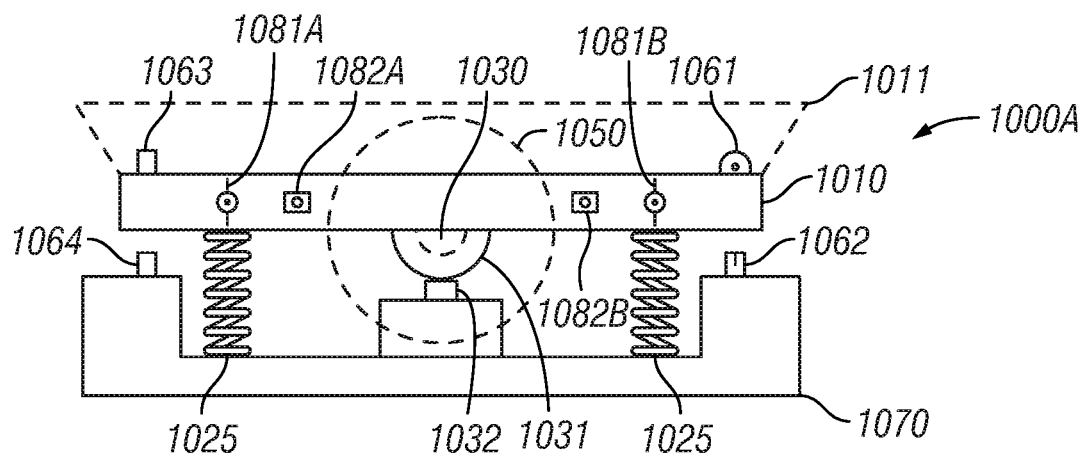
FIG. 10A illustrates a side and partially cut-away view of the navigation controller apparatus.

FIG. 10A illustrates a navigation controller apparatus 1000A that allows a user (not illustrated) to control a computing device or other digital or physical devices. For example, the navigation controller apparatus 1000A may allow for the interactive control of a computer game, or user interface elements of a display screen, and/or allow for physical interactions such as exercise or therapy from a stationary apparatus or platform such as the navigation controller apparatus 1000A. The navigation controller apparatus 1000A may include at least two footpad (s) 1010 that may move separately and/or independently of one another. In some embodiments, the footpad (s) 1010 may have a lip 1011 that surrounds them to prevent a user's foot (not illustrated) from leaving the surface of the footpad 1010 when the navigation controller apparatus 1000A is in use.

The footpad (s) 1010 may have an axle 1030 that passes through the at least a portion of the body of the footpad(s) 1010. The axle 1030 may be supported and/or coupled to a magnet 1031. In at least one example, the magnet 1031 may couple to the footpad(s) 1010. The magnet 1031 may allow the movement of the footpad(s) 1010 to be detected by a sensor 1032. The sensor 1032, in at least one embodiment, is a Hall effect sensor. In some embodiments, the magnet 1031 may alternatively be a light source, or some other electric or magnetic field emitting device or element that can be monitored by the sensor 1032. The sensor 1032 may be coupled to a computing device 1033. The computing device 1033 may connect to a display or interface device (not illustrated) that is configured to receive information from the navigation controller apparatus 1000A.

The footpad(s) 1010 may also include one or more sensors on and/or within the footpad(s) 1010. The sensors may include a foot detection sensor 1061, a foot enabled sensor 1063, and/or other sensors configured to allow detection and interaction with a user and the footpad 1010. The foot detection sensor 1061 (or foot sensor) may be beam interruption, range detection, pressure detection, or other sensors and/or circuits that would allow for a computing device to know when and/or how a user's foot (not illustrated) has interacted with the footpad(s) 1010. The foot enabled sensor 1063 may be switch(s), pressure detection, directional detection, and/or other sensors and/or circuits that would allow when and/or how an action is to occur.

In at least one embodiment, the axle 1030 may be supported by a wheel 1050 or other form of stanchion. The wheel 1050, and/or a wheel like stanchion may also be supported by a base 1070. The base 1070 can also provide support to the spring(s) 1025. In at least one example, the wheel 1050 supports the footpad(s) 1010 and/or the axle 1030. In at least one embodiment, the spring(s) 1025 can provide resistance and/or support to the footpad(s) 1010 keeping them at a first or neutral position until a user causes the footpad(s) 1010 to be repositioned to a second position (toe up or toe down). In at least one example, a first position would have the footpad(s) 1010 parallel to a surface supporting the navigation controller apparatus 1000A, while a second position would place the footpad(s) 1010 at an angle positive or negative of a line that is parallel to a surface supporting the navigation controller apparatus 1000A. In another example, a first position would have the footpad(s) 1010 at a first angle to a surface supporting the navigation controller apparatus 1000A, while a second position would increase or decrease the angle of the footpad(s) 1010 positively or negatively from the first angle. It would be understood that the footpad(s) may be placed in any number of positions, and could include a third position, a fourth position, a fifth position, and additional positions. In some embodiments, the resistance provided by the springs may be adjusted to allow for increased pressure and/or resistance to a user's interaction.

The base 1070 may also provide support for sensors that can assist in determining the position of the footpad(s) 1010. The sensor 1062, and/or sensor 1064 may be a switch(s), light detector(s), distance measuring, pressure sensing, and/or other sensing and/or measurements devices or circuits. For illustration purposes, FIG. 10A shows sensor 1062 as a measurement sensor and sensor 1064 as a switch. It would be understood that different sensors may be used individually, and/or in combination.

In at least one embodiment, the footpad(s) 1010 may house at least one feedback device 1081A and/or 1081B (collectively 1081) for haptic feedback. The haptic feedback may be in response to actions in a virtual reality environment, and/or may come from a remote computing device such as a game server or entertainment system. In some examples, the haptic feedback may be a response to an action or trigger from one of the various sensors of the navigation controller apparatus 1000A. The feedback device (s) 1081 may be a motor, vibration motors, and/or other actuation devices. In some embodiments, the footpad(s) 1010 may also house at least one tilt sensor 1082A and/or 1082B (collectively 1082) that allow for additional sensing of various movements of the footpad(s) 1010. For example, the footpad(s) 1010 may be tilted and/or rotated in a +/−Y direction, +/−X direction, and/or in +/−Z direction all of which could be sensed with a tilt sensor 1082. In at least one example, the tilt sensor 1082 is an accelerometer and/or other motion or position sensing device.

Figure 10B:
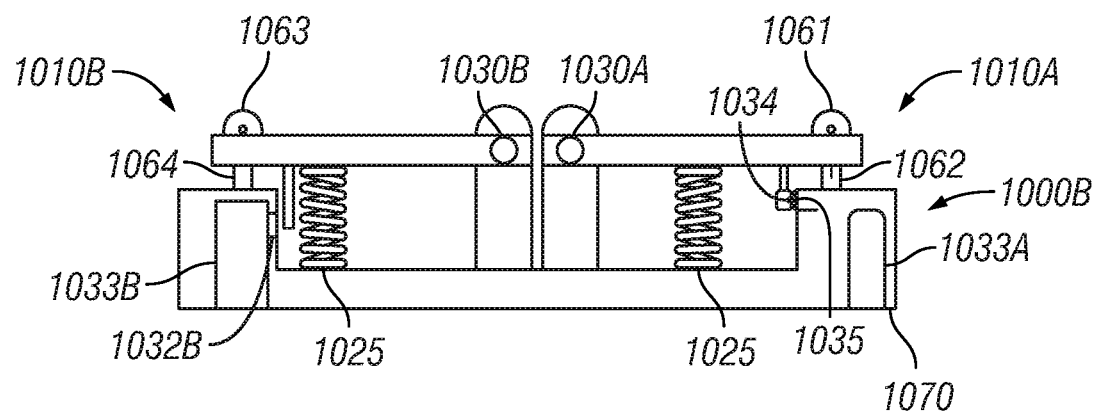
FIG. 10B illustrates a side and partially cut-away view of the navigation controller apparatus.

FIG. 10B illustrates a navigation controller apparatus 1000B allowing for control of a computing device or other digital or physical devices. The navigation controller apparatus 1000B can include footpad 1010A and footpad 1010B. In at least one embodiment, the footpad(s) 1010A and/or 1010B are positioned in a manner that is mirrored. For example, a first footpad 1010A may be raised at what can be called the toe end 1012A of the navigation controller apparatus 1000B, while the second footpad 1010B is raised at what can be the heel end 1012B of the navigation controller apparatus 1000B. The footpads 1010A and/or 1010B may be lower at their opposing ends 1013A and/or 1013B. In at least one embodiment, the footpads 1010A and/or 1010B can be rotatable around an axis 1030A and/or 1030B. The axis 1030A and/or 1030B can be a fixed point around which the footpads 1010A and/or 1010B can rotate. The axis 1030A and/or 1030B can each have a magnet 1031 surrounding and/or coupling to them. The magnet 1031 may allow for the detection of movement by footpad 1010A and/or 1010B with a sensor 1032. In at least one embodiment, the sensor 1032 is a Hall effect sensor. In other embodiments, the magnet 1031 may be a light source, electric field, or other magnetic field emitting device or circuit. The sensor 1032, in some embodiments may be capable of reading and/or receiving from a light source, electric field, or other magnetic field emitting devices or circuits. In at some examples, the footpad(s) 1010 may be coupled to a gear 1034. The gear 1034 may be rotatable coupled to a measurement device 1035. In at least one embodiment, the measurement device 1035 is a potentiometer, or other rotational measurement device. The measurement device 1035 may also be coupled to a computing device 1033A.

In some embodiments, spring(s) 1025 may support one or more sides or ends of the footpad(s) 1010A and/or 1010B. The footpad(s) 1010A and/or 1010B may also include one or more sensors on and/or within the footpad(s) 1010A and/or 1010B. The sensors may include a foot detection sensor 1061, a foot enabled sensor 1063, and/or other sensors configured to allow detection and interaction with a user and the footpad 1010A and/or 1010B. The foot detection sensor 1061 may be beam interruption, range detection, pressure detection, or other sensors and/or circuits that would allow for a computing device to know when and/or how a user's foot (not illustrated) has interacted with the footpad(s) 1010A and/or 1010B. The foot enabled sensor 1063 may be switch(es), pressure detection, directional detection, and/or other sensors and/or circuits that would allow when and/or how an action is to occur.

The sensors may also be coupled to one or more computing devices 1033A and/or 1033B. In at least one example, the computing device(s) may be housed within the base 1070. The base 1070 can provide support to the spring(s) 1025, and one or more of the sensor(s). In some embodiments, the base 1070 may also provide support for a stanchion or other element that supports the axis 1030A and/or 1030B.

Figure 11A:
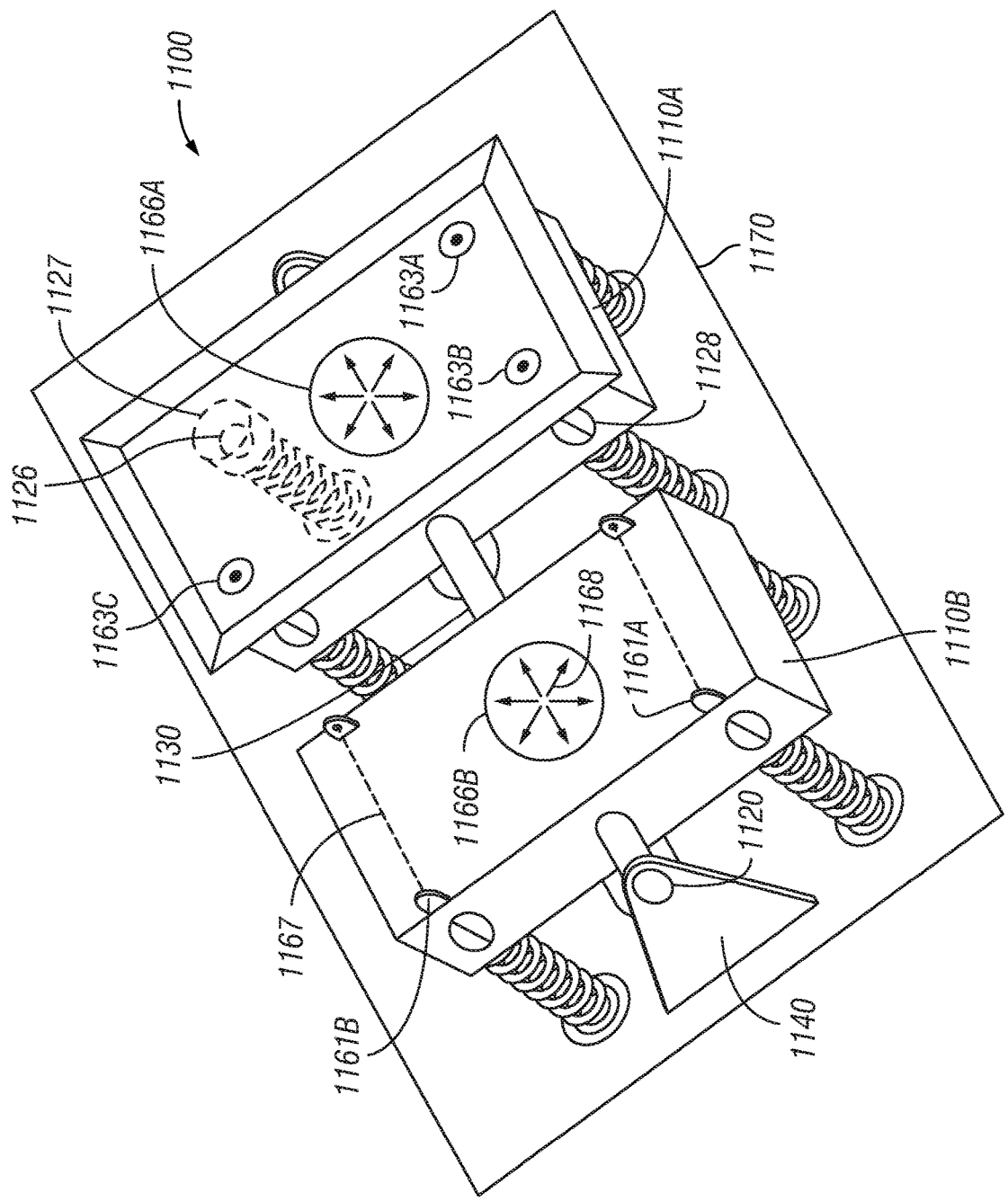
FIG. 11A illustrates a perspective and partially cut-away view of the navigation controller apparatus.

FIG. 11A is an illustration of a footpad apparatus 1100A. The navigation controller apparatus 1100A may include a first footpad 1110A and a second footpad 1110B (collectively 1110). The footpad(s) 1110 may have a lip 1111 to assist a user (not illustrated) in maintaining contact with the navigation controller apparatus 1100. In at least one embodiment, the lip 1111 may have sensor(s) along it and/or within it that can detect motion and/or other actions by a user that allow for interactions with the device. In at least one example, the footpad(s) 1110 can have sensors within and/or on their surface to allow for interactions. The sensors may include interactive or enablement sensors 1163A and/or 1163B, and/or 1163C, and/or detection sensors 1161A and/or 1161B.

In at least one example, the detection sensors 1161A and/or 1161B may be a beam interruption, range detection, pressure detection, or other sensors and/or circuits that would allow for a computing device to know when and/or how a user's foot (not illustrated) has interacted with the footpad(s) 1110. Similarly, the interaction and/or enablement sensors 1163A and/or 1163B, and/or 1163C can be switch(s), pressure detection, directional detection, and/or other sensors and/or circuits that would allow when and/or how an action is to occur. Additionally, the footpad(s) 1110 may also include a directional sensor 1166A and/or 1166B (collectively 1166). The directional sensor(s) 1166A and/or 1166B can allow a user (not illustrated) to indicate directional changes without having to remove their foot from the navigation controller apparatus 1100. For example, a user (not illustrated) that utilizes the navigation controller apparatus in a gaming environment may need to manipulate the viewing angle or direction of a character, the user could use their feet to cause the viewing angle to move by moving a directional sensor 1166A and/or 1166B without requiring a locomotion movement within the VR and/or gaming environment. It would be understood that in one example, a locomotion movement may also cause a change in the viewing angle due to a change in a character's location, or facing direction, while the directional sensor(s) 1166 would allow for a change of viewing angle without changing the character's location, or facing direction. Additionally, the directional sensor(s) 1166 may be used to generate commands and/or movement of other elements such as alerions of remote control devices, control system for a remote control device, and/or robotic limbs for robotic devices. For example, a user may utilize the footpad(s) 1110 to actuate the up and/or down motions, and/or the rotational direction of the robot, like a fixed or mobile robot, while the directional sensor(s) 1166 can allow for the control of individual limbs of the robot as selected and/or commanded by the user (not illustrated) through interactions with the navigation controller apparatus and/or a local or remote computer system (not illustrated). In another example, a user may utilize the footpad(s) 1110 to control the movements of a fixed robot such as a manufacturing robot, or may utilize the footpad(s) 1110 to control the locomotion of a mobile robot.

In some examples a user may utilize both of the directional sensors 1166A and/or 1166B to manipulate two points of reference, for example, the viewing direction of a character and a map position of a character. In additional examples, the directional sensor(s) 1166 may act as one or more keys on a keyboard. For example, a user may move a directional sensor 1166 in a first direction, and then move the footpad 1110 in a first direction, causing a secondary movement and/or reaction much like a user pressing a control key and/or a letter key and/or a directional or arrow key, or a combination or sequence of keys. In another example, when the directional sensor 1166 is neutral, footpad 1110 movement would trigger a movement in a virtual reality, remote computing system, and/or an entertainment system, but when the directional sensor 1166 is moved then movement of the footpad(s) 1166 may cause keyboard or mouse like actions to occur such as, but not limited to, a keyboard action for a mapped key, or a mouse click when the footpad 1110 is rotated in a specific direction in combination with a specific directional movement 1068 of the directional sensor 1166. Altogether the various positions of rotation of one or both directional sensor(s) 1166 may be detected and combined to determine an action or command. These actions or commands may be used to control a variety of activities within the virtual reality application such as adjusting a view (panning sideways or up or down, or zooming in or out), ascending or descending (while moving or not moving), jumping, swinging, controlling weapons or tools, opening doors, picking up items or interacting in any way. The motions of the directional sensor(s) 1166 could also be used to control a variety of movements and actions of a motor-driven device such as a robot, drone, wheelchair, or other remote control device. A movement or position change of the directional sensor(s) 1166 may be combined with a movement or position change of the one or both footpad(s) 1110 to trigger additional action or commands.

The navigation controller apparatus 1100 can include an axle 1130 that can pass through and/or traverse at least a portion of the footpad(s) 1110. In at least one example, the footpad(s) 1110 may have an aperture through which the axle 1130 can pass allowing the footpad(s) to have at least one axis of rotational freedom. The axle 1130 may be supported by one or more stanchions 1140. The stanchions 1140 may be coupled to a base, or in some embodiments may be free standing to support the navigation controller apparatus 1100. The footpad(s) 1110, in at least one example, can be supported by one or more resistive devices 1125. In at least one embodiment, the one or more resistive devices are springs, and/or adjustable springs. The resistive devices 1125 may be adjustable through an opening and/or aperture 1128 of the footpad(s) 1110. The opening and/or aperture 1128 can also allow for adjustments to be made to the resistive devices 1125. For example, in at least one example, the resistive device 1125 may have a ball and/or sphere 1126 (or other geometric object) that is capable of being received by and/or within a detection receptacle 1127. The receptacle 1127 can be configured with a sensor to know when the ball and/or sphere 1126 has been received and/or when it has reached the maximum distance it can travel within the receptacle 1127. In at least one example, the ball and/or sphere 1126, and receptacle 1127 can be combined with other sensing devices to know when the footpad(s) 1110 are in a neutral position or anywhere in between. The combination of the ball and/or sphere 1126 and receptacle 1127 allows for the detection of when the footpad(s) 1110 have reached their maximum travel distance for that axis of freedom.

Figure 11B:
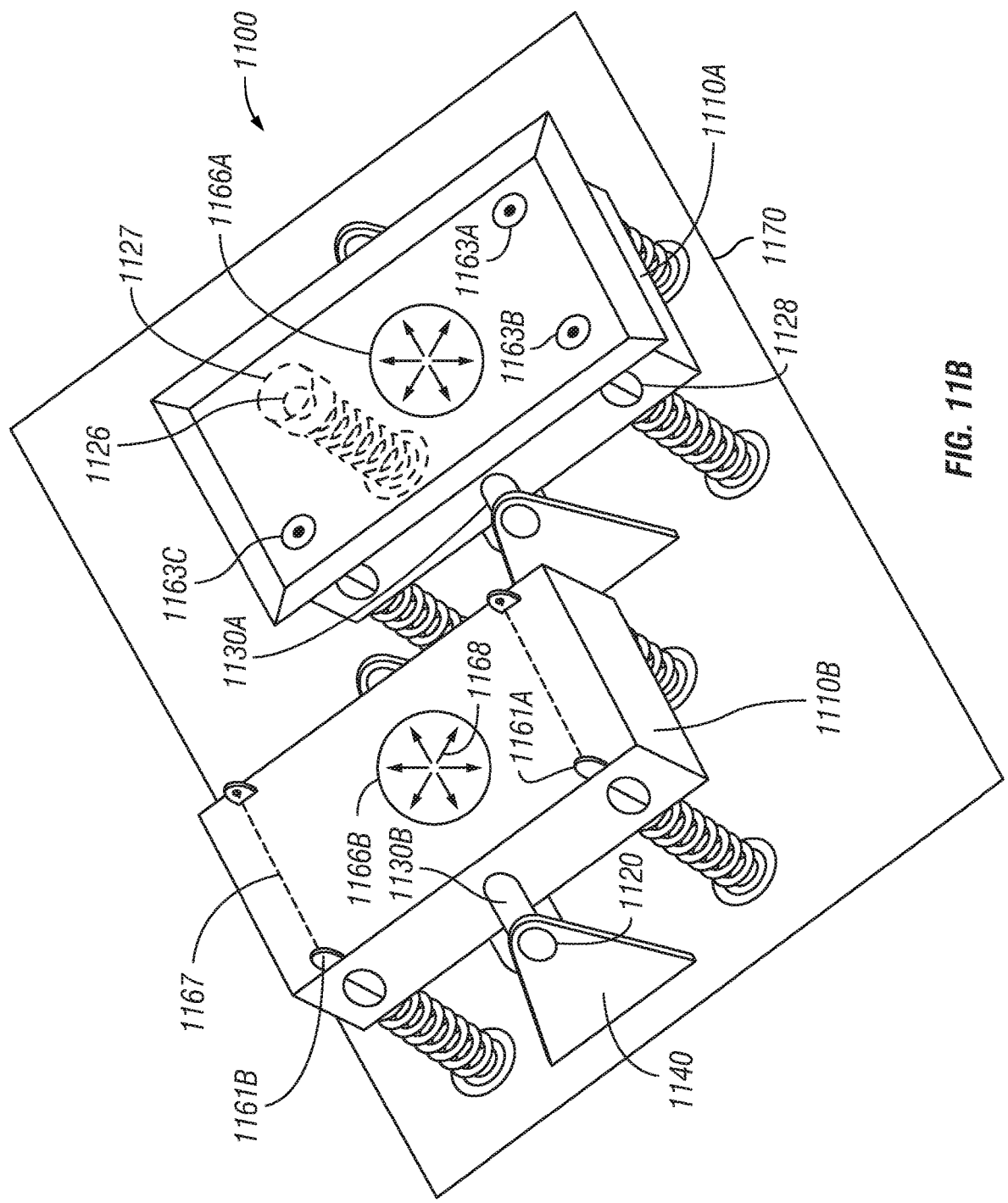
FIG. 11B illustrates a perspective and partially cut-away view of the navigation controller apparatus with staggered footpads.

FIG. 11B is an illustration of a navigation controller apparatus 1100B. The navigation controller apparatus 1100B may include a first footpad 1110A and a second footpad 1110B (collectively 1110). The footpad(s) 1110 may have a lip 1111 to assist a user (not illustrated) in maintaining contact with the navigation controller apparatus 1100B. In at least one embodiment, the lip 1111 may have sensor(s) along it and/or within it that can detect motion and/or other actions by a user that allow for interactions with the device. In at least one example, the footpad(s) 1110 can have sensors within and/or on their surface to allow for interactions. The sensors may include interactive or enablement sensors 1163A and/or 1163B, and/or 1163C, and/or detection sensors 1161A and/or 1161B.

In at least one example, the detection sensors 1161A and/or 1161B may be a beam interruption, range detection, pressure detection, or other sensors and/or circuits that would allow for a computing device to know when and/or how a user's foot (not illustrated) has interacted with the footpad(s) 1110. Similarly, the interaction and/or enablement sensors 1163A and/or 1163B, and/or 1163C can be switch(s), pressure detection, directional detection, and/or other sensors and/or circuits that would allow when and/or how an action is to occur. Additionally, the footpad(s) 1110 may also include a directional sensor 1166A and/or 1166B (collectively 1166). The directional sensor(s) 1166A and/or 1166B can allow a user (not illustrated) to indicate directional changes without having to remove their foot from the navigation controller apparatus 1100B. For example, a user (not illustrated) that utilizes the navigation controller apparatus in a gaming environment may need to manipulate the viewing angle or direction of a character, the user could use their feet to cause the viewing angle to move by moving a directional sensor 1166A and/or 1166B without requiring a locomotion movement within the VR and/or gaming environment. It would be understood that in one example, a locomotion movement may also cause a change in the viewing angle due to a change in a character's location, or facing direction, while the directional sensor(s) 1166 would allow for a change of viewing angle without changing the character's location, or facing direction. Additionally, the directional sensor(s) 1166 may be used to generate commands and/or movement of other elements such as alerions of remote control devices, control system for a remote control device, and/or robotic limbs for robotic devices. For example, a user may utilize the footpad(s) 1110 to actuate the up and/or down motions, and/or the rotational direction of the robot, like a fixed or mobile robot, while the directional sensor(s) 1166 can allow for the control of individual limbs of the robot as selected and/or commanded by the user (not illustrated) through interactions with the navigation controller apparatus and/or a local or remote computer system (not illustrated). In another example, a user may utilize the footpad(s) 1110 to control the movements of a fixed robot such as a manufacturing robot, or may utilize the footpad(s) 1110 to control the locomotion of a mobile robot.

In some examples a user may utilize both of the directional sensors 1166A and/or 1166B to manipulate two points of reference, for example, the viewing direction of a character and a map position of a character. In additional examples, the directional sensor(s) 1166 may act as a one or more keys on a keyboard. For example, a user may move a directional sensor 1166 in a first direction, and then move the footpad 1110 in a first direction, causing a secondary movement and/or reaction much like a user pressing a control key, and/or a letter key, and/or a directional or arrow key, or a combination or sequence of keys. In another example, when the directional sensor 1166 is neutral, footpad 1110 movement would trigger a movement in a virtual reality, remote computing system, and/or an entertainment system, but when the directional sensor 1166 is moved then movement of the footpad(s) 1166 may cause keyboard or mouse like actions to occur such as, but not limited to, a keyboard action for a mapped key, or a mouse click when the footpad 1110 is rotated in a specific direction in combination with a specific directional movement 1068 of the directional sensor 1166. Altogether the various positions of rotation of one or both directional sensor(s) 1166 may be detected and combined to determine an action or command. These actions or commands may be used to control a variety of activities within the virtual reality application such as adjusting a view (panning sideways or up or down, or zooming in or out), ascending or descending (while moving or not moving), jumping, swinging, controlling weapons or tools, opening doors, picking up items or interacting in any way. The motions of the directional sensor(s) 1166 could also be used to control a variety of movements and actions of a motor-driven device such as a robot, drone, wheelchair, or other remote control device. A movement or position change of the directional sensor(s) 1166 may be combined with a movement or position change of the one or both footpad(s) 1110 to trigger additional action or commands.

The navigation controller apparatus 1100B can include a first axle 1130A that can pass through and/or traverse at least a portion of the footpad 1110A, and/or a second axle 1130B that can pass through and/or traverse at least a portion of the footpad 1110B. Collectively, the axle(s) may be referred to as axle 1130. In at least one example, the footpad(s) 1110 may have an aperture through which the axle 1130 can pass allowing the footpad(s) to have at least one axis of rotational freedom. The axle 1130 may be supported by one or more stanchions 1140. The stanchions 1140 may be coupled to a base, or in some embodiments may be free standing to support the navigation controller apparatus 1100. The footpad(s) 1110, in at least one example, can be supported by one or more resistive devices 1125. In at least one embodiment, the one or more resistive devices are springs, and/or adjustable springs. The resistive devices 1125 may be adjustable through an opening and/or aperture 1128 of the footpad(s) 1110. The opening and/or aperture 1128 can also allow for adjustments to be made to the resistive devices 1125. For example, in at least one example, the resistive device 1125 may have a ball and/or sphere 1126 (or other geometric object) that is capable of being received by and/or within a detection receptacle 1127. The receptacle 1127 can be configured with a sensor to know when the ball and/or sphere 1126 has been received and/or when it has reached the maximum distance it can travel within the receptacle 1127. The combination of the ball and/or sphere 1126 and receptacle 1127 allows for the detection of when the footpad(s) 1110 have reached their maximum travel distance for that axis of freedom. With respect to FIGS. 11A and 11B, the navigation controller apparatus may be seen by a computer system as a Human Interface Device (HID) using a standard or proprietary HID protocol in emulation of a joystick, gamepad, keyboard, and/or mouse. For example, a movement detected by the navigation controller apparatus would cause transmission of joystick movements to a display screen or system.

Figure 12:
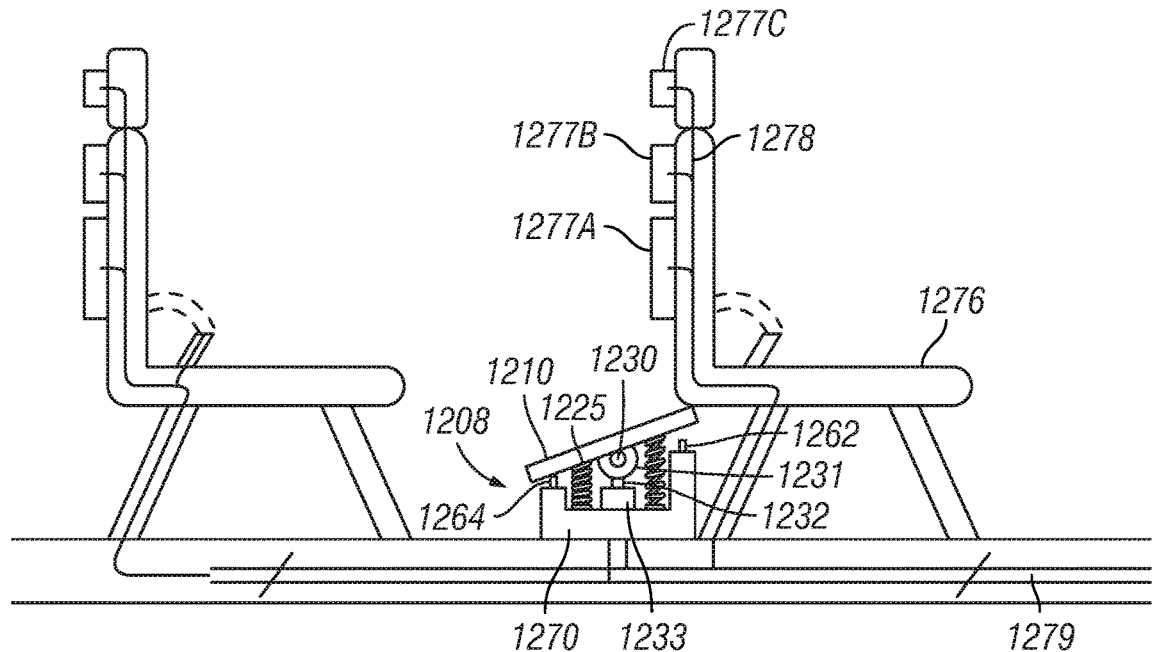
FIG. 12 illustrates a side view of a navigation controller apparatus in an entertainment environment.

FIG. 12 is an illustration of a navigation controller apparatus or system for use in a therapy and/or entertainment environment. For example, on long airplane flights the risk of Deep Vein Thrombosis (DVT) can greatly increase if a passenger (not illustrated) does not move on a regular basis. In at least one example, the navigation controller apparatus may couple with an in-flight entertainment system 1277A and/or 1277B, and/or 1277C (collectively 1277). The in-flight entertainment system 1277A and/or 1277B, and/or 1277C may include various displays, user interface, and/or computing devices which may be coupled 1278 to a central electrical and/or control system 1279 of the aircraft. The navigation controller apparatus may be coupled to a floor and/or other fixed object of an aircraft. For example, the navigation controller apparatus can be coupled to an aircraft seat 1276, in which an inflight entertainment system 1277A and/or 1277B, and/or 1277C may be located. In other example, the base 1270 of the navigation controller apparatus may be fixed and/or coupled to the aircraft floor or seat 1276. As a user (not illustrated) operates the footpad(s) 1210 around an axle 1230, the movements may be captured and/or recorded with a magnet 1231, and Hall effect sensor 1232. The movement capture device (magnet 1231 and Hall effect sensor 1232) may include other electrical, light, wave, and/or magnetic fields that can be captured and/or recorded by a sensor that may be coupled to a computing device 1233. The movement capture device may capture and/or record the rotational movement and/or change of position of the footpad(s) 1210 within their range of motion.

In some embodiments, the footpad(s) 1210 may have sensors 1262 and/or 1264 that alert a computing device, such as the computing device 1233. In some embodiments, the computing device may be contained within and/or supported by the base 1270. In at least one example, the footpad(s) 1210 may also be supported by resistive devices 1225. The resistive devices 1225 may be adjustable, and in one embodiment may be springs. As a user (not illustrated) utilizes the navigation controller apparatus the resistance of the footpad 1210 movement may need to be modified to allow the user to increase their workout and/or therapy. This may be done via a computing device and/or user interface.

In at least one embodiment, a navigation controller apparatus in combination with the seat 1276 may allow for a user (not illustrated) to utilize the entertainment systems 1277 and/or other display system to control other devices. For example, the navigation controller apparatus may be utilized by an airman to control a drone or other aircraft remotely from a control aircraft. In other examples, the seat 1276 may be a chair or other seating device that allows a user to be seated while controlling a remote control device such as a robot, drone, quad-copter, aircraft, boat, and/or vehicle. In at least one of the said examples, a user may utilize the navigation controller apparatus to control the speed and height of a drone while utilizing a controller (not illustrated) to control other aspects of the drone flight.

In at least one embodiment, the navigation controller apparatus may also be configured to operate as a mouse, gamepad, joystick, and/or certain keyboard actions for a computer and/or other computing device. This would allow a user (not illustrated) who has lost an arm or leg to utilize the navigation controller apparatus on the floor or a table in conjunction with a computer and/or computing device. The navigation controller apparatus can be used for therapeutic uses and may allow for a user to exercise each leg, foot, ankle, knees, and/or toes individually or collectively through different positioning and/or exercises. The independent and/or separated configuration of the footpad(s) 1210 allow for individual measurement and/or exercise of various limbs, muscles, tendons, and/or ligaments. Some of the motions and/or exercise the navigation controller apparatus may allow for are flexion, extension, pronation, supination, eversion, and inversion.

In some examples, the entertainment systems 1277 may be tablets, mobile computing devices, laptops, phones, or other computing devices configured and/or capable of user interaction. Additionally, the navigation controller apparatus may have motors or other actuators that are capable of providing haptic or vibrational feedback. The feedback may in some examples serve as reminders for a user to exercise and/or utilize the device. In other examples, the feedback can be utilized as a training tool to provide a user with haptic information regard the next action as determined by the computing device or other remote computing device running a computer executable program and/or code from a machine readable media. Other visual and/or auditory signals may be provided through the entertainment system 1277 or other computing devices coupled to the navigation controller apparatus. In some examples, the navigation controller apparatus may be coupled to a chair base. In other examples, the navigation controller apparatus can be placed and/or secured to a footrest that is coupled to a chair and/or the base of a chair to allow the navigation controller apparatus to rotate with the chair as it rotates.

Figure 13:
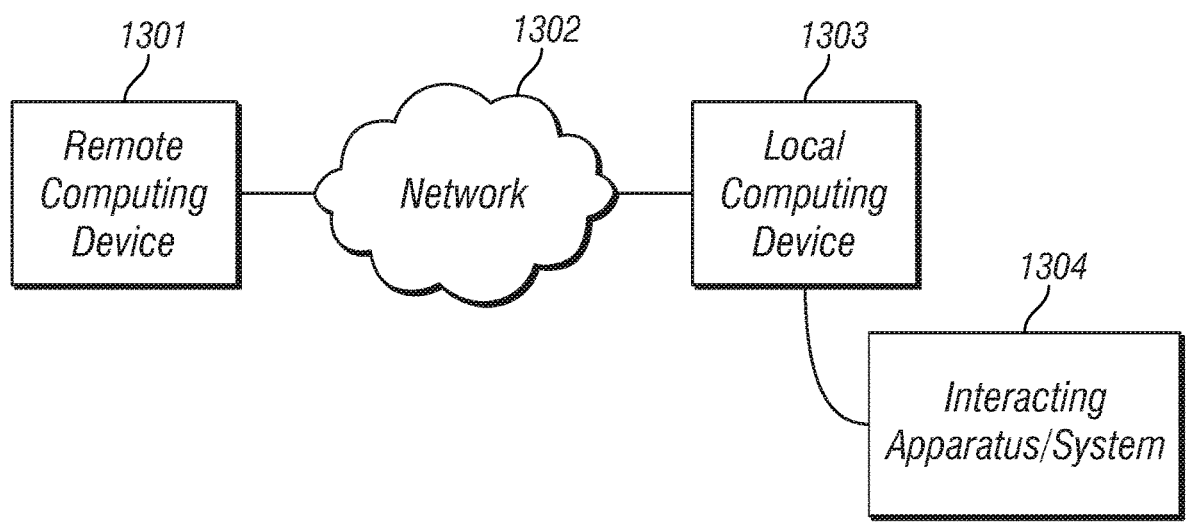
FIG. 13 illustrates network interactions of the navigation controller apparatus.

FIG. 13 illustrates a network interaction of the navigation controller apparatus. For example, the navigation controller apparatus may have a local computing device 1303 that can connect with a user interface or interaction apparatus and/or system 1304. In at least one embodiment, this connection may be between the navigation controller apparatus and a phone or other device capable of displaying and/or controlling aspects of the navigation controller apparatus. Additionally, the local computing device 1303 may connect through a network 1302 to a remote computing device 1301. The remote computing device 1301 may be a server. For example, the remote computing device 1301 may be a server for the game Fortnight™ that can then interact via the network 1302 with the local computing device 1303 and/or interacting apparatus and/or system 1304. In at least one example, the local computing device 1303 and/or interaction apparatus and/or system 1304 may have motors, and/or other actuators that can be activated by actions that occur from events stored and/or occurring on the remote computing device 1301. In at least one embodiment, the remote computing device 1301 may configure the local computing device 1303 and/or interacting apparatus and/or system 1304 through a wired or wireless network 1302.

Another example may have a user (not illustrated) running into a wall in a game running on the remote computing device 1301 and being displayed and/or interacted with by the interacting apparatus and/or system 1304 and/or the local computing device 1303 that may activate a motor or actuator when the user runs into the wall in the gaming environment to give tactile feedback of actions. Similarly, if the user is operating a motored device in the game, a motor on the navigation controller apparatus may also operate to give the user a simulated motion and/or vibration of actual movement. In some examples, the remote computing device 1301 may be a drone, robot, and/or other remote control vehicle or device, that is connected over a network 1302 to a local computing device 1303 to an interacting apparatus and/or system 1304 such as the navigation controller apparatus. In some examples, the local computing device 1303 may be a mobile or cellular phone. In other examples, the remote computing device 1301 may be an entertainment system and/or tablet coupled to a local computing device 1303 through a network 1302. In another example, the local computing device 1303 may be housed within the navigation controller apparatus and/or can be another computing device such as, but not limited to a cell phone, mobile phone, and/or tablet that can connect to a computing device housed within the interacting apparatus and/or system 1304. It would be understood that the remote computing device 1301 may include at least one computing device or at least one remote computing device. Additionally, the local computing device may include at least one computing device or at least one local computing device. The navigation controller apparatus, and/or system may be utilized for interactivity or with interactivity system such as gaming system, entertainment system, therapy system, arcade system, computing system, and/or virtual reality (VR) system.

Additionally, it would be understood that a browser or program could be implemented on a mobile device, such as, a phone, a mobile phone, a cell phone, a computer, a tablet, a laptop, a mobile computer, a personal digital assistant ("PDA"), a processor, a microprocessor, a micro controller, or other devices or electronic systems capable of connecting to a user interface and/or display system such as a computing device.

The present disclosure may also comprise a computing device that can include any of an application specific integrated circuit (ASIC), a microprocessor, a microcontroller, a digital signal processor (DSP), a field-programmable gate array (FPGA), or equivalent discrete or integrated logic circuitry such as but not limited to a Central Processing Unit. In at least one embodiment, the central processor unit could include an ASIC, microprocessor, microcontroller, DSP, FPGA, or other discrete or integrated logic circuits. In some examples, the system may include multiple components, such as any combination of one or more microprocessors, one or more microcontrollers, one or more DSPs, one or more ASICs, or one or more FPGAs. It would also be understood that multiples of the circuits, processors, or controllers could be used in combination or in tandem, or multithreading.

The components of the present disclosure may include any discrete and/or integrated electronic circuit components that implement analog and/or digital circuits capable of producing the functions attributed to the systems, methods, or modules herein. For example, the components may include analog circuits, e.g., amplification circuits, filtering circuits, and/or other signal conditioning circuits. The components may also include digital circuits, e.g., combinational or sequential logic circuits, memory devices, etc. Furthermore, the modules may comprise memory and/or storage devices that may include computer-readable instructions that, when executed cause the modules to perform various functions attributed to the modules herein.

Memory may include any volatile, non-volatile, magnetic, or electrical media, such as a random access memory (RAM), dynamic random access memory (DRAM), static random access memory (SRAM), read-only memory (ROM), non-volatile RAM (NVRAM), electrically-erasable programmable ROM (EEPROM), flash memory, hard disks, or any other digital media. Additionally, there may also be a tangible non-transitory computer readable medium that contains machine instructions, such as, a (portable or internally installed) hard drive disc, a flash drive, a compact disc, a DVD, a zip drive, a floppy disc, optical medium, magnetic medium, solid state medium, or any other number of possible drives or discs, that are executed by the internal logic of a computing device. It would be understood that the tangible non-transitory computer readable medium could also be considered a form of memory, storage device, or storage media.

Other embodiments of the locomotion apparatus may be used to navigate drones, robots, or other types of device requiring locomotion and navigation. These embodiments may be used with an augmented reality system, or any other type of currently available or later developed system for viewing or simulating an environment.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a particular sequence for execution of the steps. Such method steps may therefore be performed in a sequence other than recited unless the particular claim expressly states otherwise.

Additional Description

The following paragraphs are offered as further description of the various embodiments of the disclosed invention.

In a first embodiment, novel aspects of the present disclosure describe a virtual reality locomotion apparatus comprising: a stanchion for supporting two footpads, wherein the two footpads rotate on an axis passing through the stanchion; a plurality of sensors that detect the rotation of each footpad; and a controller transmitting signals from the plurality of sensors representing the rotation of each footpad to a virtual reality system.

In another aspect of the first embodiment, novel aspects of the present disclosure describe a virtual reality locomotion apparatus comprising: a stanchion for supporting two footpads, wherein the two footpads rotate on an axis passing through the stanchion; a plurality of sensors that detect the rotation of each footpad; and a controller transmitting signals from the plurality of sensors representing the rotation of each footpad to a virtual reality system, and one or more limitations selected from the following list:
wherein the system further comprises a second stanchion for supporting the two footpads, wherein the axis also passes through the second stanchion;
wherein the system further comprises an illusory wheel attached to a first end of the stanchion;
wherein the system further comprises a plurality of environmental simulators;
wherein at least one of the environmental simulators comprises vibrators;
wherein at least one of the environmental simulators comprises fans;
wherein at least one of the environmental simulators comprises speakers;
wherein the system further comprises a central rotatable post wherein, the plurality of sensors detect rotation of the central rotatable post and the controller transmits signals representing the rotation of the central rotatable post to the virtual reality system;
wherein the controller receives output signals from the virtual reality system to actuate the environmental simulators;
wherein the system further comprises a platform for the stanchion, wherein the rotation of the footpads actuates rotation of the stanchion on a platform axis perpendicular to the platform.

In a second embodiment, novel aspects of the present disclosure describe a method for virtual reality locomotion, comprising: stabilizing footpads of a virtual reality locomotion apparatus using motors controlled by a locomotion controller; detecting the rotation of the footpads on an axis passing through the footpads via sensors of the footpads that detect rotation of the footpads; and transmitting a digital representation of the rotation of the footpads to a virtual reality system.

In another aspect of the second embodiment, novel aspects of the present disclosure describe a method for virtual reality locomotion, comprising: stabilizing footpads of a virtual reality locomotion apparatus using motors controlled by a locomotion controller; detecting the rotation of the footpads on an axis passing through the footpads via sensors of the footpads that detect rotation of the footpads; and transmitting a digital representation of the rotation of the footpads to a virtual reality system; and one or more limitations selected from the following list:
wherein the method further comprises calibrating signals from the sensors of the footpads;
wherein the method further comprises detecting and analyzing weight and balance distribution of a user, when the user stands on the footpads, using the sensors;
wherein the method further comprises actuating a plurality of environmental simulators upon receiving instructions from the virtual reality system;
wherein at least one of the environmental simulators comprises vibrators;
wherein at least one of the environmental simulators comprises fans;
wherein at least one of the environmental simulators comprises speakers;
wherein the virtual locomotion apparatus comprises a stanchion for supporting two footpads;
wherein the method further comprises rotating the virtual locomotion apparatus on a stationary platform in response to the rotation of the footpads;
wherein the method further comprises transmitting a digital representation of rotation of a central locomotion post to the virtual reality system.

The invention claimed is:

1. A navigation controller apparatus for interactivity comprising:
   two separate footpads configured for independent movement in relation to one another, wherein the two separate footpads allow for a user's body part to be laced on each of the two separate footpads;
   at least one sensor coupled to each footpad for detecting a movement of each of the two separate footpads;
   a computing device configured for receiving and transmitting signals from the at least one sensor;
   wherein the two separate footpads are configured to be coupled to a stationary base through a mechanical means and the mechanical means positions the two separate footpads in the same plane relative to the stationary base and allows for independent movement of the two separate footpads about at least one point for each of the two separate footpads, wherein the independent movement is a vertical movement relative to the stationary base.

2. The navigation controller apparatus of claim 1, wherein the navigation controller apparatus further comprises a rotating base coupled to the stationary base through a mechanical rotational coupling allowing the stationary base to rotate in relation to the rotating base wherein the rotating base remains stationary in relation to earth.

3. The navigation controller apparatus of claim 1, wherein each of the two separate footpads further comprises at least one switch.

4. The navigation controller apparatus of claim 1, wherein each of the two separate footpads further comprise at least one foot sensor for detecting a user's foot.

5. The navigation controller apparatus of claim 4, wherein at least one foot sensor is configured to transmit signals to the computing device.

6. The navigation controller apparatus of claim 1, wherein the computing device is a local computing device configured to transmit and receive signals from a remote computing device.

7. The navigation controller apparatus of claim 1, wherein one or more of the two separate footpads has at least one haptic device.

8. The navigation controller apparatus of claim 1, wherein the mechanical means includes at least one spring, a stanchion configured to receive an axel, or a combination of at least one spring and a stanchion configured to receive an axel.

9. A method of interactivity utilizing a navigation controller apparatus comprising:
stabilizing two separate footpads through mechanical means;
detecting a movement of one of the two separate footpads with at least one sensor, wherein the two separate footpads allow for a user's body part to be placed on each of the two separate footpads; and transmitting and receiving signals with at least one computing device;
wherein the navigation controller apparatus is configured to be coupled to a stationary base through a mechanical means and the mechanical means positions the two separate footpads in the same plane relative to the stationary base and allows for independent movement of the two separate footpads about at least one point for each of the two separate footpads, wherein the independent movement is a vertical movement relative to the stationary base.

10. The method of interactivity of claim 9, wherein the mechanical means includes at least one spring, a stanchion configured to receive an axel, or a combination of at least one spring and a stanchion.

11. The method of interactivity of claim 9, wherein the mechanical means includes at least one motor, at least one gear, or a at least one motor configured to engage with at least one gear.

12. The method of interactivity of claim 9, wherein detecting further comprises detecting the movement with a Hall effect sensor and a magnet.

13. The method of interactivity of claim 9, wherein the method further comprises detecting a position of one or more of the two separate footpads with at least one switch.

14. An interactivity system comprising:
two footpads that are separated and independently movable from one another and configured to couple to a base through a mechanical means, wherein the two footpads allow for a user's body part to be placed on each of the two separate footpads and the mechanical means positions the two footpads in the same plane above a stationary base and allows for independent movement of the two footpads about at least one-point for each of the two footpads, wherein the independent movement is a vertical movement relative to the stationary base;
each footpad having at least one sensor for detecting movement of the footpad, wherein a change of positions of one of the two footpads from a neutral position is detected by the at least one sensor;
at least one local computing device configured to be coupled to the at least one sensor of each footpad, and configured to transmit and receive signals; and
at least one remote computing device configured for transmitting and receiving signals from the at least one local computing device.

15. The interactivity system of claim 14, wherein the at least one sensor is a Hall effect sensor.

16. The interactivity system of claim 14, wherein each of the two footpads further comprise at least one feedback device.

17. The interactivity system of claim 16, wherein the at least one feedback device is a motor.

18. The interactivity system of claim 16, wherein the at least one feedback device receives signals from the at least one local computing device and the at least one remote computing device.

19. The interactivity system of claim 14, wherein the at least one remote computing device transmits signals to the at least one local computing device that can transmit signals to a feedback device of each of the two footpads.

20. The interactivity system of claim 14, wherein the at least one remote computing device comprises a remote control device.

21. The interactivity system of claim 14, wherein the at least one remote computing device comprise an entertainment system.

22. The interactivity system of claim 14, wherein the interactivity system is used for control of remote controlled devices.

23. The interactivity system of claim 14, wherein the interactivity system is used for therapy of a human body.

* * * * *